(12) United States Patent
Buehler et al.

(10) Patent No.: US 8,445,734 B2
(45) Date of Patent: *May 21, 2013

(54) PHOTOLABILE PROTECTIVE GROUPS FOR IMPROVED PROCESSES TO PREPARE OLIGONUCLEOTIDE ARRAYS

(75) Inventors: Sigrid Buehler, Waldkraiburg (DE); Markus Ott, Kraiburg (DE); Wolfgang Pfleiderer, Constance (DE)

(73) Assignee: NIGU Chemie GmbH, Waldkraiburg (DE)

( * ) Notice: Subject to any disclaimer, the term of this patent is extended or adjusted under 35 U.S.C. 154(b) by 38 days.

This patent is subject to a terminal disclaimer.

(21) Appl. No.: 12/792,122

(22) Filed: Jun. 2, 2010

(65) Prior Publication Data
US 2010/0292458 A1    Nov. 18, 2010

Related U.S. Application Data

(62) Division of application No. 10/764,989, filed on Jan. 26, 2004, now Pat. No. 7,759,513.

(60) Provisional application No. 60/449,070, filed on Feb. 21, 2003.

(51) Int. Cl.
*C07C 205/19*    (2006.01)
*C07H 21/02*    (2006.01)
*C07H 21/04*    (2006.01)

(52) U.S. Cl.
USPC ...... 568/939; 568/932; 536/25.31; 536/25.34

(58) Field of Classification Search
USPC .................... 568/939, 932; 536/25.31, 25.34
See application file for complete search history.

(56) References Cited

U.S. PATENT DOCUMENTS

| | | | |
|---|---|---|---|
| 5,143,854 | A | 9/1992 | Pirrung et al. |
| 5,489,678 | A | 2/1996 | Fodor et al. |
| 5,635,608 | A | 6/1997 | Haugland et al. |
| 5,763,599 | A | 6/1998 | Pfeiderer et al. |
| 6,153,744 | A | 11/2000 | Pfeiderer et al. |
| 6,900,231 | B2 | 5/2005 | Pan et al. |

FOREIGN PATENT DOCUMENTS

| | | |
|---|---|---|
| DE | 19938092 | 2/2001 |
| WO | WO 9405153 A1 * | 3/1994 |
| WO | WO 98/39348 | 9/1998 |
| WO | WO 02/20150 | 3/2002 |
| WO | WO 02/062747 | 8/2002 |

OTHER PUBLICATIONS

Patani et al. Chem. Rev., 1996, 96, p. 3147-3176.*
Yip et al. J. Phys. Chem., 1985, 89, p. 5328-5330.*
Nifantev et al., Russian Chemical Reviews, 1994, 63(7), p. 575-609.*
McGall et al., Proc. Natl. Acad. Sci. USA, 1996, 93, p. 13555-13560.*
Hasan, A., et al., "Photolabile Protecting Groups for Nucleosides: Synthesis and Photodeprotection Rates," Tetrahedron, vol. 53, No. 12, 1997, pp. 4247-4264.
Avino et al. (1996) Bioorganic & Medicinal Chemistry 4(10):1649-1658.
Eritja et al. (1992) Tetrahedron 48(20):4171-4182.
Buhler et al. Helvetica Chimica Acta, 2004, 87, p. 620-659.
Walbert et al. Helvetica Chimica Acta, 2001, 6, p. 1601-1611.
Forbes et al. Can. J. Chem. 1958, 36, p. 869-878.
Wagner, P.J. Am. Chem. Soc. 1967, 89(12), p. 2820-2825.
Adam et al. J. Chem. Soc. 1930, 9202-206.
Machine translation of DE 19938092, provided by EPO, http://ep/espacenet.com/, accessed online on Apr. 29, 2008.
Barone et al. (2001) Nucleosides, Nucleotides & Nucleic Acids 20:525-531.
Beaucage and Iyer (1992) Tetrahedron 48:2223-2311.
Beier and Hoheisel (2000) Nucleic Acid Res. 28:e11.
Chee et al. (Oct. 25, 1996)Science 274:610-614.
Fahim and Fleifel (1952) J. Chem. Soc. 4519-4521.
Fodor et al. (Feb. 15, 1991) Science 251:767-773.
Giegrich et al. (1998) Nucleosides & Nucleotides 17:1987-1996.
Hasan et al. (1997) Tetrahedron 53:4247-4264.
McGall et al. (Jun. 4, 1997) J. Am. Chem. Soc. 119:5081-5090.
Nuwaysir et al. (2002) Genome Research 12:1749-1755.
Pirrung and Bradley (1995) J. Org. Chem. 60:1116-1117.
Singh-Gasson et al. (Oct. 1999) Nature Biotech. 17:974-978.
Walker et al. (1988) J. Am. Chem. Soc. 110:7177.
Woll et al., Poster Presentation on the EuroBiochips 2002.

* cited by examiner

*Primary Examiner* — Shaojia Anna Jiang
*Assistant Examiner* — Jonathan S Lau
(74) *Attorney, Agent, or Firm* — Oblon, Spivak, McClelland, Maier & Neustadt, L.L.P.

(57) ABSTRACT

The present invention discloses novel and improved nucleosidic and nucleotidic compounds that are useful in the light-directed synthesis of oligonucleotides, as well as, methods and reagents for their preparation. These compounds are characterized by novel photolabile protective groups that are attached to either the 5'- or the 3'-hydroxyl group of a nucleoside moiety. The photolabile protective group is comprised of a 2-(2-nitrophenyl)-ethyoxycarbonyl skeleton with at least one substituent on the aromatic ring that is either an aryl, an aroyl, a heteroaryl or an alkoxycarbonyl group. The present invention includes the use of the aforementioned compounds in light-directed oligonucleotide synthesis, the respective assembly of nucleic acid microarrays and their application.

19 Claims, 6 Drawing Sheets

PHOTOLABILE PROTECTIVE GROUPS FOR IMPROVED PROCESSES TO PREPARE OLIGONUCLEOTIDE ARRAYS

FIELD OF THE INVENTION

The present invention relates to photolabile compounds, reagents for preparing them and methods for their use as photocleavable protective groups, particularly in the synthesis of high density arrays of oligonucleotides on solid support.

BACKGROUND OF THE INVENTION

Synthetic nucleic acid microarrays have gained tremendous importance in the analysis of nucleic acid samples from biological sources. They are powerful tools that are suitable for the analysis of complex mixtures of nucleic acids as required in the biological and biomedical sciences. Applications of microarrays include research with the aim to understand the correlation of gene sequences with their function, the analysis of the expression pattern of various organisms and tissues that can be employed in drug discovery, the analysis of genetic variation that occurs between individuals, which is employed in the development of individual medicines, and the analysis of mutation patterns that occur in specific tissues, which is useful in cancer research and diagnosis. Another application of is the use of microarrays to sequence nucleic acids by the analysis of the hybridization pattern obtained from a particular nucleic acid sequence on an array. As almost all analysis techniques that are based on nucleic acid hybridization can be performed using nucleic acid microarrays there are numerous other important applications of the microarrays and new applications continue to emerge.

In applications of nucleic acid microarrays, the surface bound oligonucleotides of the arrays (probes) are used to analyze sample sequences (targets) through complementary recognition (hybridization) in a parallel fashion. Driven by the complexity of the nucleic acid sequence information in biological samples and the value of the usually small biological samples there is an increasing demand for microarrays with miniaturized features that allow a highly parallel analysis of such small samples. This demand is best met through the light-directed synthesis of microarrays for the parallel, in situ assembly of oligopeptides and oligonucleotides on supports as originally described by e.g., Fodor et al. (1991) Science 251:767-773; Pirrung et al., U.S. Pat. No. 5,143,854; and Chee et al. (1996) Science 274:610-614. Due to its rapid advancement to date this approach allows the construction of feature sizes of $2.1 \times 10^{-4}$ $\mu m^2$ and possibly even smaller, as described by Singh-Gasson et al. (1999) Nature Biotech. 17:974-978. In contrast, microarrays that are assembled by spotting prefabricated oligonucleotides or cDNA samples onto surfaces allow the fabrication of feature sizes of about 75 $\mu m^2$, as reviewed for example in Bowtell and Sambrook, eds., "DNA Microarrays: A Molecular Cloning Manual," Cold Spring Harbor Laboratory Press (2002). Due to the easy and flexible spatial addressing of reaction sites on the support, a further advantage of light-directed array assembly is that it can be performed in a parallel and automated fashion.

In order to become more widely used microarrays must be available at reasonable cost, which is driven by various factors including the consumption of reagents in their manufacturing, the degree of automation employed and the throughput of manufactured arrays obtained in the production set-up. Since microarrays from light directed synthesis are built sequentially on the array surface by a multitude of chemical processes, it is of utmost importance to optimize the individual steps employed in order to increase the throughput.

Light-directed syntheses of microarrays largely rely on the conventional, highly optimized schemes for the synthesis of oligonucleotides on solid supports exploiting the phosphoramidite chemistry as described e.g. by Beaucage et al. (1992) Tetrahedron 48:2223-2311, which is incorporated herein by reference in its entirety. They comprise the stepwise attachment of nucleoside synthons activated by a phosphoramidite group, in a predetermined order to either, depending on the direction of chain extension, the 5'-functional group or the 3'-functional group of the growing strand, which is linked to a support such as the surface of a DNA chip. Each elongation step usually consists of a reaction cycle including the deprotection of either the 5'- or the 3'-hydroxyl group of the growing strand, chain extension by addition of a nucleoside phosphoramidite and an activator, the optional capping of unreacted terminal hydroxyl groups, and the oxidation of the newly formed internucleosidic phosphorous linkage to the pentavalent state. Arrays comprising oligonucleotide probes assembled in the 5' to 3' direction are suitable for assays relying on hybridization, as well as assays involving enzymatic reactions, e.g. elongation or ligation, since the 3'-ends of its oligonucleotide probes are freely accessible, as described by Beier et al. (2001) Helv. Chim. Acta 84:2089-2095.

Since all of the reactions of a chain extension cycle, apart from the deprotection step, are basically carried out according to well-elaborated conventional methods and involve the use of vast excesses of reagents, they are essentially quantitative. In the light-directed microarray assembly of oligonucleotides, the step of removing the standard acid-labile dimethoxytrityl (DMT) protective group is replaced by the photochemical removal of a light sensitive protective groups, which is the limiting reaction with respect to the efficiency and duration of the elongation cycle. Thus, for the commonly used [(α-methyl-2-nitropiperonyl)-oxy]carbonyl (MeNPOC) protective group the yield of the photochemical deprotection on the support in the "dry" mode, i.e. without solvent, is only about 90%, resulting in a cycle efficiency of less than 90% as described by Barone et al. (2001) Nucleosides, Nucleotides & Nucleic Acids 20:525-531 and McGall et al. (1997) J. Am. Chem. Soc. 119:5081-5090, each of which is incorporated herein by reference in its entirety. Such conversion rates are rather moderate compared to the standard technology employing DMT-protection, leading to the formation of failure sequences and to truncated oligonucleotide probes, with the desired full-length sequences representing in case of an array with 20-mer probes only about 10% of the total.

Furthermore, removal of the MeNPOC group in the dry state requires irradiation times of about 1 minute or longer if the deprotection is performed in the presence of a solvent. For each elongation step in the synthesis of an oligonucleotide array four photolytic steps are necessary, corresponding to the coupling steps, which are subsequently performed with each of the four nucleotidic synthons in pre-defined areas on the support. The total time needed for deprotection adds up to 4×N minutes for the assembly of an array of N-mers. Thus, in order to achieve higher throughput rates of array assembly short deprotection times are crucial.

The photocleavage of MeNPOC-protected nucleosides proceeds most rapidly under dry conditions or in less polar solvents, such as toluene or dioxane. Additionally, the resulting yields and the corresponding coupling efficiencies are moderate at most as discussed above. In contrast, the also widely-used 2-(2-nitrophenyl)-propoxycarbonyl (NPPOC) group requires irradiation times that are significantly longer in a dry state, but much shorter in polar solutions, such as mixtures of water with acetonitrile or methanol, as described by Giegrich et al. (1998) Nucleosides & Nucleotides 17:1987-1996. Further enhanced deprotection rates for NPPOC-nucleosides were accomplished by Beier et al. (2000) Nucleic Acids Res. 28:e11, via irradiation in acetonitrile containing a small amount of a base, such as DBU or NMI. This method provides up to 12% higher cycle efficiency than the application of MeNPOC-protected phosphoramidites in a dry deprotection format.

Early reports on photocleavable protective groups in nucleoside and nucleotide chemistry were related to the ethers and carbonate esters of the ortho-nitrobenzyl group including derivatives thereof, as described by Pillai, in *Organic Photochemistry*, Ed. Padwa, Marcel Dekker, NY and Basel, 1987, Vol. 9, p. 225-323 and Walker et al. (1988) J. Am. Chem. Soc. 110:7170-7177. The MeNPOC protective group can be considered as an advanced variant in this category.

Pyrenylmethoxycarbonyl-type protective groups have also been used as described by McGall and Rava, International Patent Application Publication No. WO 98/39348. The respective nucleoside and nucleotide derivatives of the aforementioned protective groups, although resulting in arrays of sufficient quality for certain applications, have unsatisfactory deprotection rates and yields. Additionally, upon cleavage of the ortho-nitrobenzyl compounds undesired side products like toxic nitrosophenyl compounds are formed.

Enhanced cleavage rates and/or reduced levels of side products have been observed for dimethoxybenzoin carbonates as described by Pirrung and Bradley (1995) J. Org. Chem. 60:1116-1117, and for both ortho-nitrophenylethyl-type carbonates, such as the above described NPPOC, and ortho-nitrophenylethyl-type sulfonates as described by Hasan et al. (1997) Tetrahedron 53:4247-4264; Giegrich et al. (1998) Nucleosides & Nucleotides 17:1987-1996; and Pfleiderer et al., U.S. Pat. Nos. 5,763,599 and 6,153,744. The former photolabile group displays faster deprotection rates, whereas the two latter groups also display higher deprotection yields and purities. However, as discussed above, even these "second generation" photolabile protective groups there remains a need for improvement with respect to faster deprotection and higher conversion rates.

In the light of an increasing demand methods have been devised using digital light processors to manufacture gene chips having any individual design within hours as described e.g. by Singh-Gasson et al. (1999) Nature Biotech. 17:974-978. The overall throughput of such instruments, however, is currently limited to about two chips per working day, mainly due to the extensive amount of accumulated deprotection time in an array synthesis. Thus, speeding up the photolysis time would significantly cut the overall process time.

The present invention provides novel photolabile protective groups, which are well suited for both the 3'-OH— and 5'-OH function of the sugar moiety of nucleoside derivatives. The novel protective groups have improved deprotection properties allowing for significantly accelerated array assembly and enhanced oligonucleotide quality. Furthermore, the protective groups are specifically adapted to 'dry' or 'wet' deprotection conditions in order to allow high-throughput and high-quality array fabrication independent of the deprotection approach used.

SUMMARY OF THE INVENTION

The present invention includes novel photolabile protective groups, which provide faster deprotection times and enhanced conversion rates, while producing lower levels of side products. Included in the present invention are the corresponding protected nucleosidic and nucleotidic derivatives. The photolabile protective groups of the invention as well as the corresponding protected nucleosidic and nucleotidic derivatives are generally represented by the following formula:

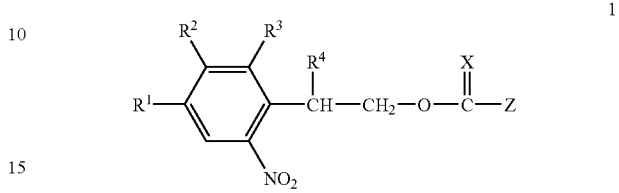

wherein $R^1$ is COOY, wherein Y is selected from the group consisting of an optionally substituted alkyl group of up to 10 carbon atoms, under the proviso that $R^2$ is selected from the group consisting of H, $NO_2$, CN, $OCH_3$ or halogen or is an optionally substituted alkyl or alkoxyl group, respectively, having up to 4 carbon atoms; or $R^1$ is selected from the group consisting of H, $NO_2$, CN, $OCH_3$ or halogen or an optionally substituted alkyl or alkoxyl group respectively, having up to 4 carbon atoms, under the proviso that $R^2$ is selected from the group consisting of an optionally substituted aryl group, an optionally substituted heteroaryl group or an optionally substituted aroyl group;

$R^3$ is selected from the group consisting of H, $NO_2$ or halogen;

$R^4$ is selected from the group consisting of H, $OCH_3$ or an optionally substituted alkyl group having up to 4 carbon atoms;

X is selected from oxygen or sulfur; and

Z is selected from the group consisting of a leaving group, a primary amine, a secondary amine, an alcohol, or deoxyribonucleoside or ribonucleoside as represented by either of the following formulae (2) or (3):

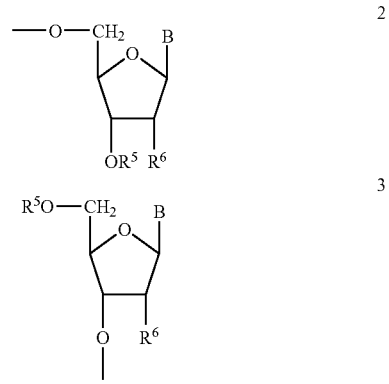

wherein $R^5$ is selected from the group consisting of H, an oligonucleotide or a functional group useful in oligonucleotide synthesis, wherein said functional group is selected from the group including, but not limited to a phosphoramidite group, preferably comprising a β-cyanoethoxy group and a diisopropyl amino group attached to the phosphorus;

$R^6$ is selected from the group consisting of H, OH or an optionally substituted alkoxyl or alkenoxyl group respectively, having up to 4 carbon atoms, or $WR^8$ wherein W is selected from oxygen or sulfur and $R^8$ is selected from a protective group useful in oligonucleotide synthesis;

B is selected from the group consisting of adenine, cytosine, guanine, thymine, uracil or chemical modifications thereof and in the case of adenosine, cytosine and guanine the amino functions on the heterocycle may bear a protective group useful in oligonucleotide synthesis; or Z is selected from the group consisting of a chemically modified deoxyribonucleoside, ribonucleoside, or an analog thereof.

In a preferred embodiment of the invention, $R^4$ is a methyl group, $R^1$ and $R^3$ are hydrogen, and $R^2$ is selected from the group consisting of aryl, heteroaryl and aroyl. In this particular embodiment, more preferably X is oxygen and $R^2$ is selected from a phenyl or benzoyl moiety.

In accordance with other preferred embodiments of the invention $R^4$ is a methyl group, $R^3$ and $R^2$ are hydrogen, and $R^1$ is selected from an alkoxy carbonyl moiety. Particularly preferred embodiments in this respect comprise compounds wherein X is oxygen and $R^1$ is a methoxy carbonyl or tert-butoxy carbonyl moiety.

The invention includes methods for the syntheses of the photolabile protective groups of the invention and for the corresponding activated derivatives thereof. In one embodiment of the invention, methods are disclosed for synthesizing alcohols of formula (4) and derivatives thereof, wherein $R^1$ through $R^4$ have the above-ascribed meanings, which are the precursors to the preferred photolabile protective groups of the invention.

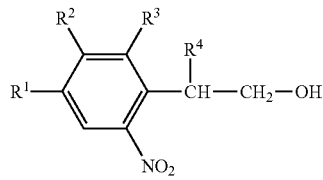

4

Included in the present invention are methods for the preparation of compounds incorporating one or more of the photolabile protective groups of the invention. The photolabile protective can be introduced to any compound containing a nucleophilic functional group including, but not limited to primary and secondary amines, alcohols and thiols. In a preferred embodiment, the photolabile protective group is introduced to the primary or a secondary hydroxyl group of a nucleoside, nucleotide or analogs thereof.

Thus, one embodiment of the present invention includes a method for derivatizing the primary hydroxyl group of a nucleoside, nucleotide or analogs thereof with a photocleavable protective group said method comprising the steps of:

a. transforming the hydroxyl group of an alcohol having the following general formula:

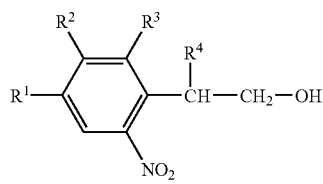

4 wherein $R^1$ through $R^4$ have the above ascribed meanings into an activated carbonate, thiocarbonate or sulfonate; and b1. reacting said activated carbonate, thiocarbonate or sulfonate with the primary hydroxyl group of a nucleoside, nucleotide or analogs thereof.

Another embodiment of the invention includes a method for derivatizing a secondary hydroxyl group of a nucleoside, nucleotide or analogs thereof with a photocleavable protective group said method comprising the steps of:

a. transforming the hydroxyl group of an alcohol having the following general formula:

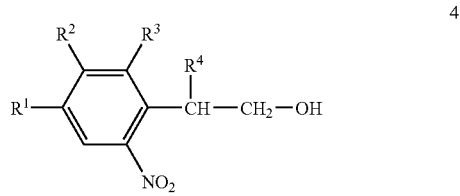

4 wherein $R^1$ through $R^4$ have the above-ascribed meanings into an activated carbonate, thiocarbonate or sulfonate;

b2. reacting said activated carbonate thiocarbonate or sulfonate with the secondary hydroxyl group of a nucleoside, nucleotide or nucleoside analog in which the primary hydroxyl group is protected and c. removing the protective group from the primary hydroxyl group.

Conversely, in an alternate embodiment of the present invention, the hydroxyl group of the nucleoside, nucleotide or analogs thereof to be protected is transformed into an activated carbonate, thiocarbonate or sulfonate, followed by reaction of the activated carbonate, thiocarbonate or sulfonate with the hydroxyl group of compound (4).

Upon conversion to the respective phosphoramidites, these compounds allow for an elongation of a growing nucleotide strand attached to a support either in the 3' to 5' or 5' to 3' direction. Therefore, also included in this invention is an improved method for the light-directed synthesis of oligonucleotides on a support by stepwise elongation either in the 3' to 5' direction employing nucleotidic building blocks featuring photocleavable protective groups at their 5'-terminus, or in the 5' to 3' direction employing such building blocks that are accordingly 3'-protected. The latter case is further specified in parentheses below. Said method is comprised of the following steps:

1. attaching a first nucleotide to a support via its 3'(5')-hydroxyl group, the 5'(3')-position of which is derivatized with a photocleavable protective group of the invention;

2. irradiating the support-bound nucleotide resulting from step 1, to remove the photocleavable protective group, thereby deprotecting the 5'(3')-hydroxyl group;

3. contacting the support-bound nucleotide obtained in step 2 in the presence of an activator with a second nucleotide comprising a 5'(3')-protective group of the invention and a 3'(5')-phosphoramidite functional group which reacts with the 5'(3')-hydroxyl group of the support-bound nucleotide forming an internucleosidic phosphorus linkage;

4. optionally capping any unreacted 5'(3')-hydroxyl groups with an inert protective group, to prevent further coupling;

5. oxidizing the newly formed internucleosidic phosphorous linkage to the naturally occurring pentavalent state;

6. optionally repeating steps 2 to 5 while successively applying the nucleoside monomers in a predetermined order until the desired oligonucleotide strand is completed; and 7. removing all nucleobase and phosphate protective groups.

The photolabile protective groups of the invention are superior over those of the prior art in terms of reduced deprotection times and enhanced cycle efficiency. They are particularly useful in the light-directed, parallel assembly of oligonucleotides on a support. Additionally, the photolabile protective groups, as well as, the corresponding reagents and nucleosidic derivatives, are accessible by straightforward and high-yielding syntheses and are easy to handle and to store. The present invention includes the use of these compounds in the preparation of oligonucleotide arrays such as gene chips. In particular, protective groups are provided that are optimized for deprotection by irradiating the support either in the dry state or immersed in a solvent, outperforming respective prior art protective groups in terms of throughput and quality of array fabrication.

DETAILED DESCRIPTION OF THE INVENTION

Figure 1A:
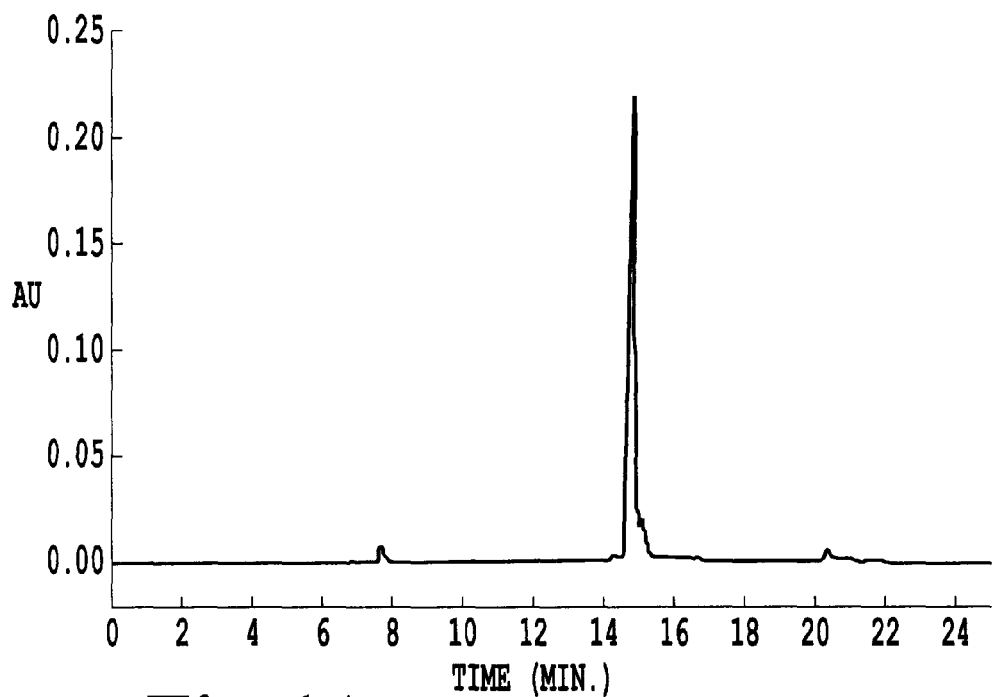
FIGS. 1A-C display HPLC chromatograms analyzing the photolysis of 5'-tBuC-NPPOC-deoxy thymidine (25) in methanol/water (1:1, v/v) upon irradiation at 365 nm as described in Example 37 after 0 seconds (FIG. 1A), 60 seconds (FIG. 1B) and 600 seconds (FIG. 1C).

The present invention includes novel photolabile protective groups, which provide faster deprotection times and enhanced conversion rates, while producing lower levels of side product. Included in the present invention are the corresponding protected nucleosidic and nucleotidic derivatives. The invention includes methods for the syntheses of the photolabile protective groups of the invention and for the corresponding activated derivatives thereof.

The photolabile protective groups of the invention are especially useful for applications in the synthesis of oligonucleotides, particularly in the light-directed preparation of microarrays comprising immobilized oligonucleotides.

Various terms are used herein to refer to aspects of the present invention. To aid in the clarification of the description of the components of the invention, the following descriptions are provided.

It is to be noted that the term "a" or "an" entity refers to one or more of that entity; for example, an oligonucleotide refers to one or more oligonucleotides. As such, the terms "a" or "an," "one or more" and "at least one" are used interchangeably herein.

The term "protective group" refers to a suitable chemical moiety that is used to protect a functional group from unwanted reactions. A protective group is attached to a functional group and removed at a later stage to reveal the intact functional group. The removal of a protective group is preferably performed under specific conditions that do not affect any other modifications of the molecule comprising said functional group. Methods for deprotection include, but are not limited to applying chemical means, such as acidic, basic or nucleophilic agents, and physical means, such as light or an electrical current. Examples of protective groups well known in the art for various functional groups are described by Greene et al., in *Protective Groups in Organic Synthesis,* 2d. Ed., John Wiley and Sons (1991), which is incorporated herein by reference in its entirety. The terms "protective group" and "protecting group" are used interchangeably herein.

The term "aryl", alone or in combination with any other term, refers to a carbocyclic aromatic radical, preferably consisting of from 6-14 carbon atoms, and more preferably consisting of from 6-10 carbon atoms. Examples of aryl radicals include, but are not limited to phenyl, naphthyl, indenyl, indanyl, azulenyl, fluorenyl, anthracenyl and the like. Aryl radicals may be optionally substituted with 1 to 3 substituents selected from the group including, but not limited to alkyl, alkoxy, halogen, hydroxyl, amino, acyl, nitro, cyano, thioalkyl and the like.

The term "heteroaryl", alone or in combination with any other term, refers to an aromatic 5- or 6-membered monocyclic radical, an aromatic 9- or 10-membered bicyclic radical, or an aromatic 11- to 14-membered tricyclic radical, provided that said monocyclic radical or at least one ring of said bicyclic or tricyclic radicals contains 1 or 2 O- and/or S-atoms and/or from 1 to 4 N-atoms, provided that the total number of heteroatoms in each ring is 4 or less. The fused rings completing said bicyclic and tricyclic radicals may contain only C-atoms and may be saturated, partially saturated, or unsaturated. Said N- and S-atoms may be oxidized and said N-atoms may be quaternized. Heteroaryl radicals are attached at any available N- or C-atom of any ring. Heteroaryl radicals may be optionally substituted with 1 to 3 substituents selected from the group including, but not limited to alkyl, alkoxy, halogen, hydroxyl, amino, acyl, nitro, cyano, thioalkyl and the like.

The term "aroyl", alone or in combination with any other term, refers to a carbonyl radical to which an aryl or heteroaryl moiety, as defined above, is bound. Examples of aroyl radicals include, but are not limited to benzoyl, naphthoyl, 2-furanoyl, 3-thiobenzoyl and the like. The carbonyl function of said aroyl radicals may be optionally derivatized as a ketal, dithioketal or monothioketal group, such as 1,3-dioxane, 1,3-dioxolane, 1,3-dithiane, 1,3-dithiolane, 1-3-oxathiane, 1-3-oxathiolane and the like. Aroyl radicals may be optionally substituted with 1 to 3 substituents selected from the group including, but not limited to alkyl, alkoxy, halogen, hydroxyl, amino, acyl, nitro, cyano, thioalkyl and the like.

The term "leaving group" as used herein refers to a chemical moiety or atom capable of being readily displaced, optionally in the presence of an auxiliary base where appropriate, by a nucleophile in a nucleophilic substitution reaction. Examples of nucleophiles include, but are not limited to amines, alcohols and thiols, their respective anions and the like. Examples of leaving groups include, but are not limited to (thio)carbonates, (thio)carbamates, halides (F—, Cl—, Br—, I—), imidazolyl, nitrophenoxyl, and the like.

As used herein the terms "nucleoside" or "nucleoside analog" mean either a deoxyribonucleoside or a ribonucleoside or any chemical modifications thereof. Modifications of the nucleosides include, but are not limited to, 2'-position sugar modifications, 5-position pyrimidine modifications, 8-position purine modifications, modifications at cytosine exocyclic amines, substitution of 5-bromo-uracil, and the like.

As used herein the term "oligonucleotide" refers to a single stranded chain of either deoxyribonucleotides or ribonucleotides or chemical modifications thereof, such as e.g. nucleotides with a 2'O-4'C-methylene bridge in their sugar portion, which are the constituting nucleotides of locked nucleic acids (LNA). Modifications include, but are not limited to, those that provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, bases that can be part of unusual base-pairing combinations such as the isobases isocytidine and isoguanidine and the like. Modifications further include attached labels and reporter molecules, such as fluorescent dyes, biotin, minor groove binders and the like that are known to those skilled in the art. In addition modifications include modified backbones of the oligonucleotides, examples being peptide nucleic acids (PNA), phosphorothioate DNA, methylphosphonate DNA and other modifications known to those skilled in the art and reviewed by Micklefield (2001) J. Current Medicinal Chemistry 8:1157-1179, which is incorporated herein by reference in its entirety. Oligonucleotides, as referred to in this invention can consist of any combinations of the nucleotides and their modifications described above and can have either a few, e.g. up to 20, or many, e.g. 20 to several hundred or more, nucleotides incorporated in their chain.

As used herein the term "solid support" refers to a material, preferably polymeric, which is insoluble in the medium employed in all unit operations performed in the course of the synthesis of oligonucleotides. The solid support can be selected from an inorganic polymer, including, but not limited to inorganic oxides such as silica, alumina, zeolites and controlled pore glass (CPG), a modified inorganic polymer, such as silica or CPG with an organic coating, e.g. aminopropylsilane derivatized silica or CPG, or an organic polymer, including, but not limited to polystyrene, polyacrylamide, polymethacrylate, polyvinylalcohol, or other synthetic polymers or other organic polymers and any copolymers, composite materials or combination of the above inorganic or organic materials. Furthermore, the solid supports are comprised of functional groups, which may or may not be introduced by derivatization, suitable to participate in the coupling reaction of an oligonucleotide synthesis. The functional groups are either unprotected, e.g. free hydroxyl groups, or protected, e.g. DMT-protected hydroxyl groups, that need to be deprotected prior to the coupling reaction. The solid support is subjected to cycles of deprotection reactions, coupling reactions with nucleotide synthons, such as e.g. phosphoramidite synthons, and eventually other chemical reactions in a stepwise manner to synthesize oligonucleotides, as described e.g. by Beaucage et al. (1992) Tetrahedron 48:2223-2311, which is incorporated herein by reference in its entirety.

In a preferred embodiment of the invention, the solid support is comprised of at least one substantially flat surface, most preferably realized by slide- or foil-like shapes. For certain embodiments, the surface of the solid support may be physically divided, e.g. to separate synthetic sites, by wells, pins, trenches or other structural elements. In other preferred embodiments, the solid support may be in the form of beads, microspheres, or other geometric configurations.

Note, that throughout this application various citations are provided. Each citation is specifically incorporated herein in its entirety by reference.

The novel photolabile protective groups of the instant invention as well as the corresponding protected nucleosidic and nucleotidic derivatives prepared therewith are generally represented by the following formula:

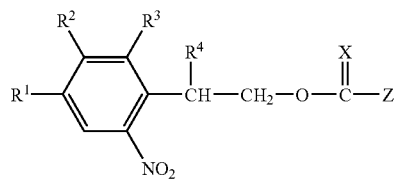

1 wherein $R^1$ is COOY, wherein Y is selected from the group consisting of an optionally substituted alkyl group of up to 10 carbon atoms, under the proviso that $R^2$ is selected from the group consisting of H, $NO_2$, CN, $OCH_3$, halogen or an optionally substituted alkyl or alkoxyl group, respectively, having up to 4 carbon atoms; or $R^1$ is selected from the group consisting of H, $NO_2$, CN, $OCH_3$ or halogen or an optionally substituted alkyl or alkoxyl group respectively, having up to 4 carbon atoms, under the proviso that $R^2$ is selected from the group consisting of an optionally substituted aryl group, an optionally substituted heteroaryl group or an optionally substituted aroyl group;

$R^3$ is selected from the group consisting of H, $NO_2$ or halogen;

$R^4$ is selected from the group consisting of H, $OCH_3$ or an optionally substituted alkyl group having up to 4 carbon atoms;

X is selected from oxygen or sulfur; and

Z is selected from the group consisting of a leaving group, a primary amine, a secondary amine, an alcohol, or deoxyribonucleoside or ribonucleoside as represented by either of the following formulae (2) or (3):

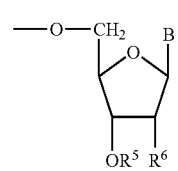

2

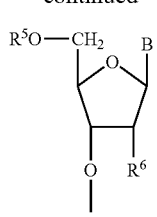

wherein
- R⁵ is selected from the group consisting of H, an oligonucleotide or a functional group useful in oligonucleotide synthesis;
- R⁶ is selected from the group consisting of H, OH or an optionally substituted alkoxyl or alkenoxyl group respectively, having up to 4 carbon atoms, or is WR⁸ wherein W is selected from oxygen or sulfur and R⁸ is selected from a protective group useful in oligonucleotide synthesis;
- B is a purine or pyrimidine base selected from the group consisting of adenine, cytosine, guanine, thymine, uracil or chemical modifications thereof and in the case of adenosine, cytosine and guanine the amino functions on the heterocycle may bear a protective group useful in oligonucleotide synthesis; or
- Z is selected from the group consisting of a chemically modified deoxyribonucleoside or ribonucleoside, or an analog thereof.

In a preferred embodiment of the invention, R⁴ is a methyl group, R¹ and R³ are hydrogen, and R² is selected from the group consisting of aryl, heteroaryl and aroyl. In this particular embodiment, more preferably X is oxygen and R² is selected from a phenyl or benzoyl moiety. Protective groups having this substitution pattern correspond to groups such as the 2-(5-phenyl-2-nitrophenyl)-1-propyloxy carbonyl (P—NPPOC) and the 2-(5-benzoyl-2-nitrophenyl)-1-propyloxy carbonyl (Bz-NPPOC) protective groups, respectively.

In accordance with other preferred embodiments of the invention R⁴ is a methyl group, R³ and R² are hydrogen, and R¹ is selected from an alkoxy carbonyl moiety. Particularly preferred embodiments in this respect comprise compounds wherein X is oxygen and R¹ is a methoxy carbonyl or tert-butoxy carbonyl moiety. Compounds having this substitution pattern correspond to groups such as the 2-(4-methoxy carbonyl-2-nitrophenyl)-1-propoxy carbonyl (MeC-NPPOC) and 2-(4-tert-butoxy carbonyl-2-nitrophenyl)-1-propoxy carbonyl (tBuC-NPPOC) protective groups.

The invention includes reagents represented by the general formula (1), wherein R¹ through R⁴ and X have the above-ascribed meanings, for incorporating the photolabile protective group into the molecule intended to be protected. Z can be any suitable leaving group capable of being displaced by the nucleophilic atom of a functional group to be protected, such as for example an oxygen of a hydroxyl group or a nitrogen of an amino group. Examples of leaving groups (Z) include, but are not limited to halo (F—, Cl—, Br—, I—), imidazolyl, nitrophenoxyl, (thio)carbonates, (thio)carbamates, and the like. Thus, said reagents can be used in applications wherein protection, particularly of hydroxyl and amino groups is required. Such applications include, but are not limited to oligonucleotide synthesis on solid support.

The invention also includes compositions of the general formula (1) wherein R¹ through R⁴ and X have the above-ascribed meanings and Z represents a building block, which is preferably monomeric and particularly useful to prepare oligo- and polynucleotides. Such building blocks include, but are not limited to nucleic acids, nucleotides, nucleosides and the like. In a preferred embodiment, the building block is selected from the group including, but not limited to ribonucleosides and deoxyribonucleosides as depicted in formulae (2) and (3) above including the appendant definitions. In another preferred embodiment, the building block is linked to the photolabile protective group via a hydroxyl or amine function. In most embodiments of the invention, said photolabile protective groups are attached to the 5'-OH or the 3'-OH of a nucleoside. In a preferred embodiment, the nucleosidic building blocks depicted by formulae (2) and (3) above are further comprised of an activating functional group R⁵ either at the 5'- or the 3'-position, wherein said functional group is selected to enable the formation of a linkage to a growing oligonucleotide chain. In one embodiment of the invention, R⁵ is a phosphoramidite group, preferably comprising a β-cyanoethoxy group and a diisopropyl amino group attached to the phosphorus. Furthermore, as well known by those skilled in the art, said activated nucleoside building blocks, also referred to herein as nucleoside synthons, may bear carbonyl based permanent protective groups on their respective amino functions of the purine and pyrimidine moieties. Preferably these groups are selected such that they can be easily removed using a base such as aqueous ammonia or ethylene diamine in ethanol. Preferred protecting groups for the primary nitrogens of the purine and pyrimidine moieties include, but are not limited to benzoyl, acetyl, DMF (dimethylformamidyl), isobutyryl, pac (2-phenoxyacetyl), ipac (2-(4-isopropylphenoxy)acetyl) and tac (2-(4-tert-butylphenoxy)acetyl) and the like.

In yet another embodiment of the invention, the nucleosidic building blocks depicted by formulae (2) and (3) above are further comprised of a 2'-substituent R⁶, wherein R⁶ represents either free, protected or derivatized hydroxyl group as defined above, and further wherein said protecting or derivatizing moieties are selected to be especially useful for the preparation of ribonucleotides or derivatives thereof. Preferred protective groups in this respect include, but are not limited to acetal and silylether groups, particularly preferred protective groups are the tetrahydropyranyl and the TBDMS group. Preferred derivatizations of said 2'-hydroxyl group include O-alkylation and O-alkenylation.

Further included in the present invention are compounds of formula (1) that are building blocks for the synthesis of modified oligonucleotides or oligonucleotide analogs, both of which are meant herein to be subsumed under the term "oligonucleotide" as defined above. Said modifications and analogs of oligonucleotides are in general characterized in that they have some structural and functional features in common with naturally occurring deoxyribonucleotides and ribonucleotides such that they allow e.g. for specific hybridization to a complimentary oligonucleotide strand. As a consequence said building blocks of the invention for the synthesis of modified oligonucleotides or oligonucleotide analogs are correspondingly modified monomeric nucleosides and nucleotides. Such modifications may refer to the sugar moiety, the nucleobase or the activating group, depending on what kind of modification in the intended oligonucleotide is to be achieved.

Included in the present invention is a method for preparing the reagents and compounds illustrated by general formula (1) above, including the attendant definitions. In particular, methods for the preparation of the photolabile protected nucleosidic building blocks as well as derivatives and analogs thereof, are disclosed wherein Z is either linked via its primary or secondary hydroxyl group, such as exemplified by formulae (2) and (3), respectively.

In one embodiment of the invention, methods are disclosed for synthesizing alcohols of formula (4), wherein $R^1$ through $R^4$ have the above-ascribed meanings, which are the preferred photolabile protective groups of the invention.

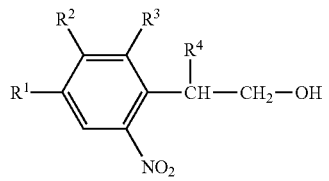

4

The methods for the synthesis of these compounds are set forth in Examples 1 through 17 as discussed in detail below.

Example 1 describes a general method for the synthesis of compounds illustrated by formula (10) starting from 3-ethylaniline (7), as depicted in Scheme 1. Briefly, subsequent to the protection of the amino function of the starting material (7) by acetylation, a nitro group is introduced in the para-position to provide the substituted nitrobenzene 9. The corresponding halo-substituted derivatives 10a-c are then obtained via diazoination and subsequent Sandmeyer reaction in 46%, 80% and 57% yield, respectively.

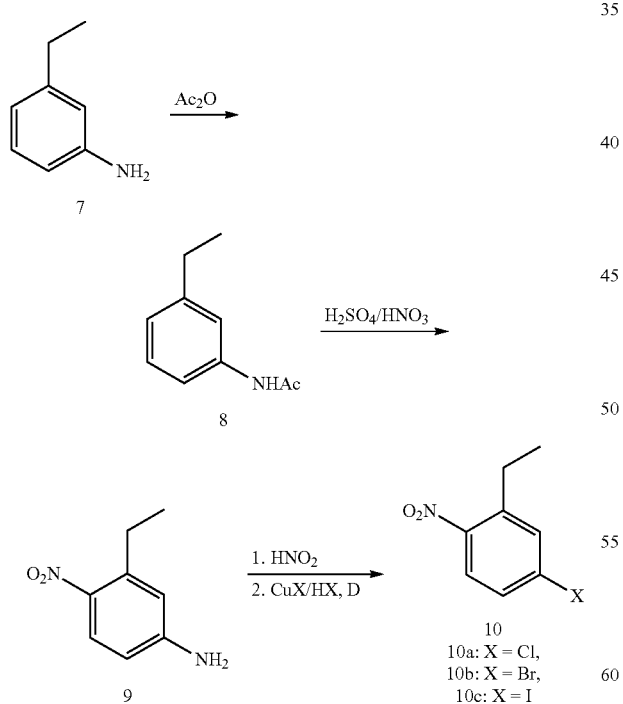

Preferred aryl-substituted compounds (11a-c) are accessible in good to excellent yields starting from compound 10b by means of the a Suzuki coupling reaction, as illustrated in Scheme 2 and described in Examples 2 through 4.

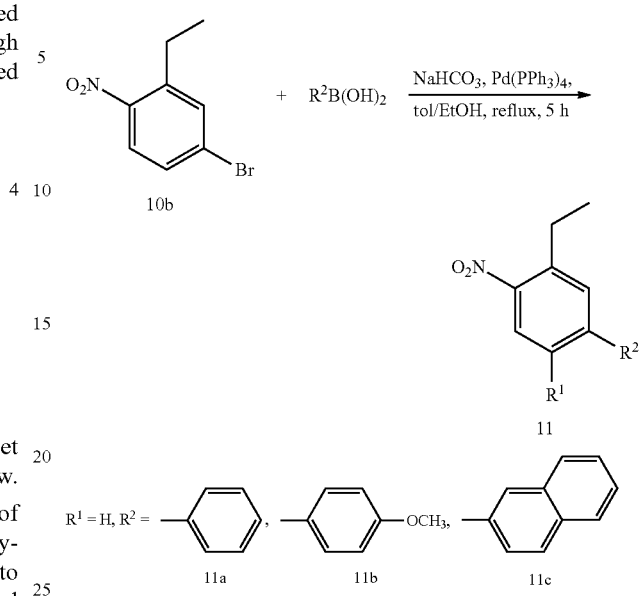

The introduction of an alkyloxycarbonyl substitutent to the 2-ethyl-nitro phenyl scaffold was achieved as outlined in Scheme 3 starting from 4-ethylbenzoic acid (12). With reference to Scheme 3, a nitration reaction, followed by esterification of the carboxyl group affords the desired compounds, as described in Examples 5 and 6 for the methyl and the tert-butyl esters 11d and e, respectively, which are preferred building blocks.

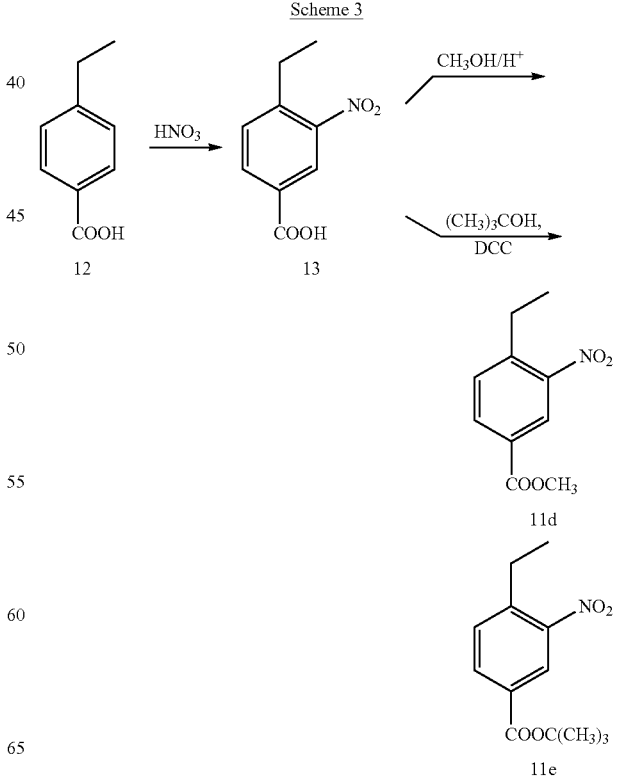

The aryl substituted compound (11f), which is a precursor to the Bz-NPPOC protective group, was synthesized as illustrated in Scheme 4 and described in Examples 7 and 8 and illustrated in Scheme 4. With reference to Scheme 4, the condensation of benzylcyanide (14) with 2-nitroethylbenzene (15) in the presence of potassium hydroxide results in the formation of the oxime (16), which is then converted into the nitro derivative (11f) by treatment with hydrogen peroxide in a boiling solution of potassium hydroxide in a methanol/water mixture.

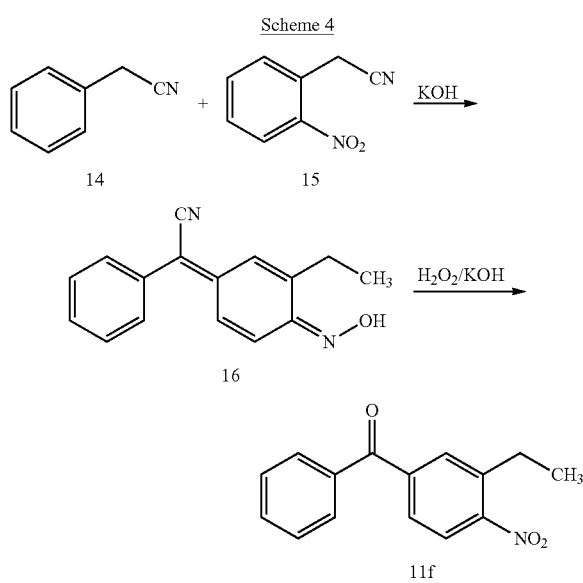

Derivatives of 11f in which the benzoyl ring is substituted with various moieties are accessible using the methods described in Examples 7 and 8 By replacing starting material 14 with the a corresponding ring-substituted benzylcyanide in the synthesis protocols of Examples 7 and 8, the respectively substituted derivatives of 11f are accessible.

Examples 9 through 14 describe the aldol condensation reactions between the 2-ethyl-nitrophenyl derivatives 11a-e and formaldehyde to yield the corresponding 2-substituted propanols of formula (4). The yields of these reactions, which are illustrated in Scheme 5, were in the range of 38% to 94%. Under these reaction conditions, the respective conversion of the benzoyl derivative 11f yielded only 24% of corresponding alcohol 4f due to the susceptibility of the carbonyl group to unwanted side reactions.

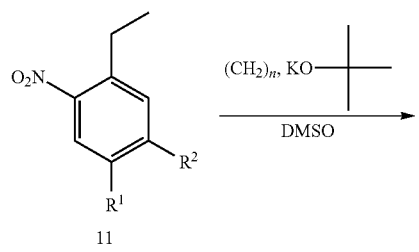

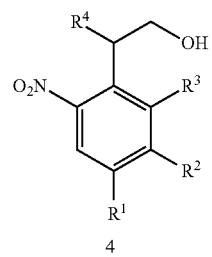

$R^3 = H$
$R^4 = CH_3$

| | $R^1$ | $R^2$ |
|---|---|---|
| 4a | H | Ph |
| 4b | H | 4'-methoxyphenyl |
| 4c | H | naphathelene |
| 4d | methoxycarbonyl | H |
| 4e | tert-butoxycarbonyl | H |

Scheme 6 illustrates an alternate synthetic route for converting benzoyl derivative 11f into the corresponding alcohol 4f as described in Examples 15 to 17. With reference to Scheme 6, the carbonyl group of compound 11f is protected as the 1,3-dioxane to provide compound 17, which is then converted via an aldol condensation using Triton B as a base into compound 18. The carbonyl group of compound 18 is then deprotected to provide compound 4f in 82% overall yield.

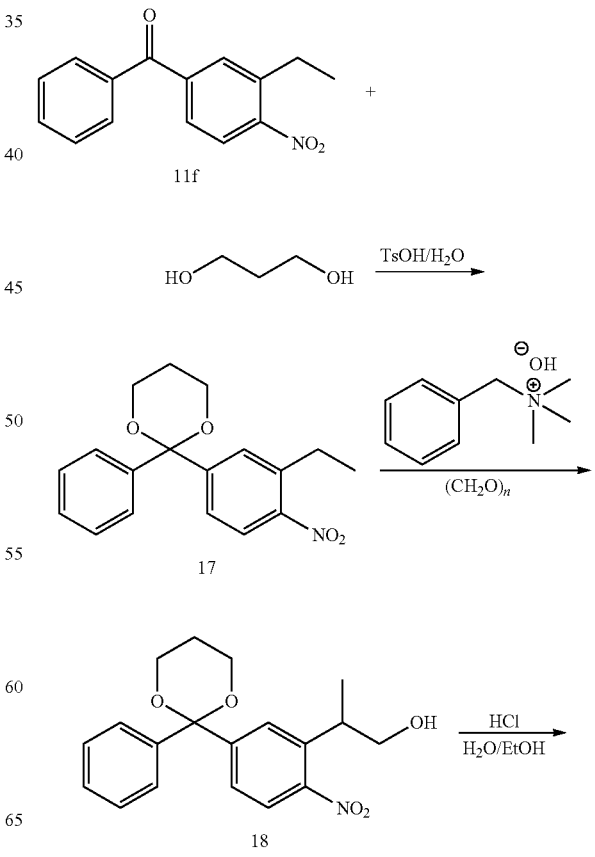

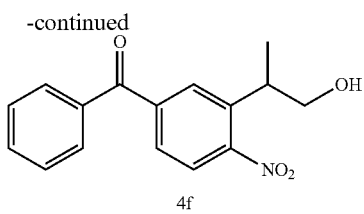

4f

Alcohols (4a-4-f) serve as preferred precursors for the photolabile protecting groups of the instant invention. Also included within the scope of the invention are derivatives of alcohols (4a-4-f). For example derivatives of alcohol 4f in which the benzylcyanide derived benzyl ring is substituted with various moieties can be obtained using the chemistry described in Examples 7 and 8 by replacing starting material 14 with the appropriately substituted benzylcyanides as noted above. Also included as preferred precursors for protective groups of the present invention are the ketal, dithioketal or monothioketal derivatives of alcohol 4f and related aroyl substituted alcohols, an example of which is compound 18 in Scheme 6.

Included in the present invention are methods for the preparation of compounds incorporating one or more of the photolabile protective groups of the invention. In a preferred embodiment, the photolabile protective group is introduced to the primary or a secondary hydroxyl group of a nucleoside, nucleotide or analogs thereof (referred to collectively hereinafter as nucleoside). As discussed in detail below, the introduction of a protective group of the invention to a secondary hydroxyl group of a nucleoside requires the intermediate blocking of the primary hydroxyl group of the nucleoside by an orthogonal protective group. In contrast, the introduction of a protective group of the invention to the primary hydroxyl group of a nucleoside can generally be achieved in the presence of an unblocked secondary hydroxyl group. The introduction of the protective group to either a primary or secondary hydroxyl group of a nucleoside is preferably accomplished by transforming either the nucleoside or compound (4) to the activated carbonate, thiocarbonate or sulfonate prior to reaction. Using either procedure, as known by one of skill in the art, an auxiliary base such as triethylamine, diisopropylethylamine, dimethylaminopyridine (DMAP) or the like is useful to facilitate the displacement of the leaving group in the course of the (thio)carbonic acid diester or sulfonic acid ester formation.

Thus, one embodiment of the present invention includes a method for derivatizing the primary hydroxyl group of a nucleoside, nucleotide or analogs thereof with a photocleavable protective group said method comprising the steps of:

a. transforming the hydroxyl group of an alcohol having the following general formula:

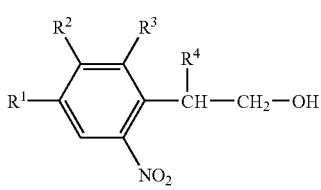

4 wherein $R^1$ is COOY, wherein Y is selected from the group consisting of an optionally substituted alkyl group of up to 10 carbon atoms, under the proviso that $R^2$ is selected from the group consisting of H, $NO_2$, CN, $OCH_3$, halogen or an optionally substituted alkyl or alkoxyl group, respectively, having up to 4 carbon atoms; or $R^1$ is selected from the group consisting of H, $NO_2$, CN, $OCH_3$ or halogen or an optionally substituted alkyl or alkoxyl group respectively, having up to 4 carbon atoms, under the proviso that $R^2$ is selected from the group consisting of an optionally substituted aryl group, an optionally substituted heteroaryl group or an optionally substituted aroyl group;

$R^3$ is selected from the group consisting of H, $NO_2$ or halogen; and $R^4$ is selected from the group consisting of H, $OCH_3$ or an optionally substituted alkyl group having up to 4 carbon atoms into an activated carbonate, thiocarbonate or sulfonate; and b1. reacting said activated carbonate, thiocarbonate or sulfonate with the primary hydroxyl group of a nucleoside, nucleotide or analogs thereof.

As noted above, in a preferred embodiment of the invention, $R^4$ is a methyl group, $R^1$ and $R^3$ are hydrogen, and $R^2$ is selected from the group consisting of aryl, heteroaryl and aroyl. In accordance with other preferred embodiments of the invention $R^4$ is a methyl group, $R^3$ and $R^2$ are hydrogen, and $R^1$ is selected from an alkoxy carbonyl moiety.

In a preferred embodiment of the invention, conversion to the activated carbonate or thiocarbonate is accomplished by reacting alcohol (4) with phosgene or derivatives or substitutes thereof, or with the respective thiocarbonyl compounds, preferably in a non-polar organic solvent at or below 25° C. Preferred phosgene derivatives include, but are not limited to diphosgene (trichoromethyl chloroformate) or triphosgene (bis-trichloromethyl chloroformate), whereas preferred substitutes for phosgene include, but are not limited to CDI (carbonyldiimidazole), bis-nitrophenyl carbonate, nitrophenoxy carbonyl chloride, pentafluorophenoxy chloroformate and the like. The reaction time required and the reaction temperatures depend on the nature of the substituents and vary from 0.5 to 6 hours at −20° C. to 25° C.

The resulting activated carbonates and thiocarbonates, respectively, as depicted by formula (1) above, wherein Z is a leaving group and all other attendant definitions are included, represent the aforementioned reagents for introducing the protective group of the invention. A general method for the preparation of these compounds is described in Example 18. They are typically obtainable in yields and purities above 90% and can generally be used without further purification, as demonstrated for the conversion of alcohols 4a, 4d and 4e as set forth in Examples 19, 20 and 21, respectively. The corresponding chlorocarbonate ester of alcohol 4f was prepared in quantitative yield applying a slightly modified procedure as described in Example 22. Subsequent to simple removal of the solvent and excess phosgene by vacuum evaporation the reaction mixture can be directly used in the next step.

In the second step (b1), the product from step (a), usually in a crude state, is then allowed to react with a nucleoside. In a preferred embodiment, the nucleoside is selected from the group of compounds having the following general formula:

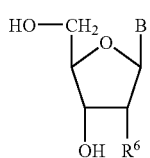

5

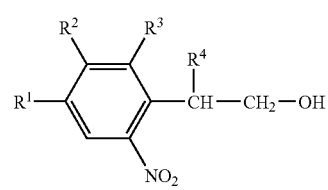

4 wherein $R^6$ is selected from the group consisting of H, OH or an optionally substituted alkoxyl dr alkenoxyl group respectively, having up to 4 carbon atoms, or $WR^8$ wherein W is selected from oxygen or sulfur and $R^8$ is selected from a protective group useful in oligonucleotide synthesis; and B is a purine or pyrimidine base selected from the group consisting of adenine, cytosine, guanine, thymine, uracil or chemical modifications thereof and in the case of adenosine, cytosine and guanine the amino functions on the heterocycle may bear a protective group useful in oligonucleotide synthesis.

A general method for introducing a photolabile protective group of the invention to a primary hydroxyl group of a nucleoside is provided in Example 23. The reaction is preferably carried out in a solvent mixture consisting of dichloromethane and a polar organic solvent optionally in the presence of a base at temperatures between −50° C. and 25° C. The polar organic solvent is selected from the group including, but not limited to DMF or pyridine. When pyridine is used as the polar organic solvent no additional base is necessary. If dichloromethane/DMF solvent mixtures are used, a base selected from the group including, but not limited to pyridine, triethylamine or ethyl diisopropylamine is added in order to scavenge the protons released during the reaction.

In a preferred embodiment of the invention, the nucleosidic compound dissolved in pyridine or DMF/base is charged and a solution of the activated carbonate, such as chlorocarbonic acid ester in dichloromethane, is added dropwise at the respective reaction temperature. The molar ratio of nucleosidic compound to activated carbonate can be adjusted according to the stoichiometry to approximately 1:1. Nevertheless, particularly if the reaction is carried out at low reaction temperatures (about −50° C.), a slight to moderate molar excess of the activated carbonate, e.g. 1.1 to 1.5 equivalents with respect to the nucleoside, may preferably be employed. If, on the other hand, the first priority is to suppress the formation of the diacylated by-products, preferably only about 0.5 equivalents of the activated carbonate are added, particularly when higher reaction temperatures of about 0° C. or higher are used.

Upon completion of the reaction (approximately 0.5 to 6 hours) and standard work-up procedures and purification, the corresponding nucleoside derivatives are obtained in good yields and high purities, as demonstrated for the syntheses of the 5'-P—NPPOC protected 2'-deoxythymidine (20) and $N^6$-tert-butyl phenoxyacetyl-2'-deoxyadenosine (21), as well as 5'-tBuC-NPPOC protected 2'-deoxythymidine (25), which are described in Examples 24, 25 and 26, respectively. The Bz-NPPOC protected $N^6$-benzoyl-2'-deoxyadenosine (29) and $N^4$-acetate-2'-deoxycytidine (30) were synthesized via the slightly modified routes described in Examples 27 and 28.

Another embodiment of the invention includes a method for derivatizing a secondary hydroxyl group of a nucleoside with a photocleavable protective group said method comprising the steps of:

a. transforming the hydroxyl group of an alcohol having the following general formula:

wherein $R^1$ is COOY, wherein Y is selected from the group consisting of an optionally substituted alkyl group of up to 10 carbon atoms, under the proviso that $R^2$ is selected from the group consisting of H, $NO_2$, CN, $OCH_3$, halogen or an optionally substituted alkyl or alkoxyl group, respectively, having up to 4 carbon atoms; or $R^1$ is selected from the group consisting of H, $NO_2$, CN, $OCH_3$ or halogen or an optionally substituted alkyl or alkoxyl group respectively, having up to 4 carbon atoms, under the proviso that $R^2$ is selected from the group consisting of an optionally substituted aryl group, an optionally substituted heteroaryl group or an optionally substituted aroyl group;

$R^3$ is selected from the group consisting of H, $NO_2$ or halogen; and $R^4$ is selected from the group consisting of H, $OCH_3$ or an optionally substituted alkyl group having up to 4 carbon atoms into an activated carbonate, thiocarbonate or sulfonate;

b2. reacting said activated carbonate, thiocarbonate or sulfonate with the secondary hydroxyl group of a nucleoside or nucleoside analog in which the primary hydroxyl group is protected and c. removing the protective group from the primary hydroxyl group.

The first step (a) of this method is identical to the first step of the method described above with respect to the protection of a primary hydroxyl group.

In the second step (b2) of this method, the product from step (a), usually in a crude state, is allowed to react as described above with a secondary hydroxyl group of a nucleoside in which the primary hydroxyl has been protected. In a preferred embodiment, the nucleoside or nucleoside analog is selected from the group of compounds having the following general formula:

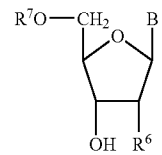

6 wherein $R^6$ is defined as above and $R^7$ is an intermediate alcohol protective group. In a preferred embodiment $R^7$ is selected from a DMT protective group or a silylether protective group, such as tert-butyldimethylsilyl (TBDMS), or selected from the group of nucleosidic and nucleotidic derivatives as well as analogs thereof accordingly comprising an intermediately protected primary hydroxyl function. The crude nucleosidic compound obtained following step (b2), which includes both the photolabile protective group of the invention, preferably as the carbonate or thiocarbonate, as well as, the intermediate protective group is optionally purified by methods known in the art.

In the third step (c) of this method, the intermediate protective group is removed, thereby releasing the primary hydroxyl function. The removal of this protective group is accomplished employing standard methods, which will depend on the intermediate protective group being removed, such as treatment with dilute acid in the case of the DMT group or with fluoride (F) in the case of silyl groups. The product is then isolated and purified according to the methods described for step (b1) above.

As noted above, in an alternate embodiment of the present invention, the hydroxyl group of the nucleoside to be protected is converted preferably into an activated carbonate, thiocarbonate or sulfonate, followed by reaction with compound (4). According to this embodiment, in the first step a nucleoside of formulae (5) or (6), including the above ascribed definitions, or a nucleosidic derivative or analog thereof, comprising either a primary or secondary hydroxyl function to be furnished with said protective group, is converted preferably into an activated carbonate, thiocarbonate or sulfonate, as described above. The activated compound is then, in the second step, treated with an alcohol of formula (4) to provide the desired photolabilely protected compound, whose primary hydroxyl group is subsequently deblocked according to the aforementioned step (c), in the case in which an intermediate protective group is employed. The corresponding synthetic procedures and reaction conditions suitable thereto can easily be deduced from those described in the aforementioned steps (a), (b1), (b2) and (c) by someone knowledgeable in the art.

This embodiment of the invention is illustrated in Example 29, which describes a method for introducing the P—NPPOC-group to the 3'-terminus of 2'-deoxythymindine. Briefly, the activated carbonate 3'-(4-nitrophenoxy carbonyl) 2'-deoxythymidine, is synthesized using methods well known in the art by reacting 4-nitrophenoxy carbonyl chloride with 5'-DMT protected 2'-deoxythymidine and subsequent removal of the DMT group. The activated carbonate is then reacted with the corresponding alcohol in the presence of dimethylaminopyridine (DMAP) to provide the derivatized product compound (27). This straightforward synthesis afforded the intended product in good yield.

According to a further embodiment of the invention, the nucleoside or nucleoside analog, which has been derivatized with a photolabile protective group either at its primary or a secondary hydroxyl group as described herein, is converted into the corresponding phosphoramidite by methods known in the art employing a suitable phosphitylation reagent. A general method for preparation of the respective phosphoramidite is provided in Example 30. Thus, subsequent to the synthesis of the phosphoramidite, a synthon useful for the light-directed synthesis of oligonucleotides is accessible. Examples 31 to 36 describe specific examples of such reactions using the phosphitylation reagent bis(diisopropylamino)-β-cyanoethoxy phosphane in the presence of either tetrazole or DCI as activator to generate the phosphoramidites of both 5'- and 3'-P—NPPOC-protected dT, as well as of 5'-tBuC-NPPOC-dT, 5'-P—NPPOC-dA(tac), 5'-Bz-NPPOC-dA(bz) and 5'-Bz-NPPOC-dC(ac). All six of these compounds include the preferred β-cyanoethoxy group and diisopropyl amino group attached to the phosphorus.

In order to evaluate light-cleavable protective groups, as well as, the corresponding deprotection processes for light-directed oligonucleotide array synthesis, the cycle efficiency and the rate of the photolytic release of 5'/3'-protective groups must be determined. The rate of photolytic deprotection of accordingly protected nucleosides in solution or in a dry state can be used to assess these parameters.

Figure 1B:
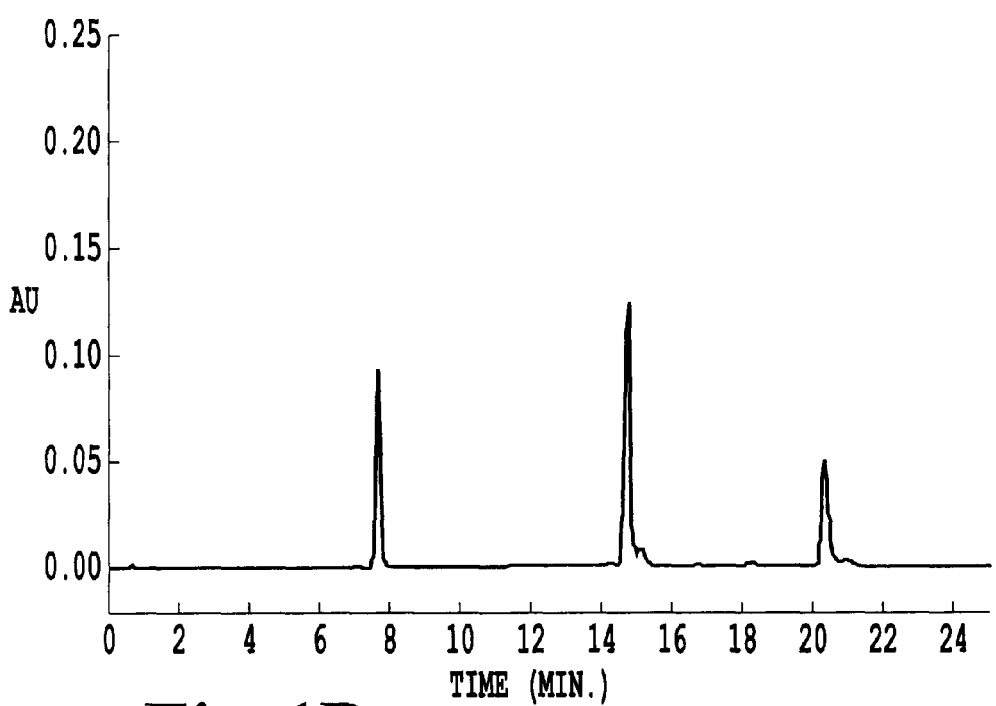
Figure 1C:
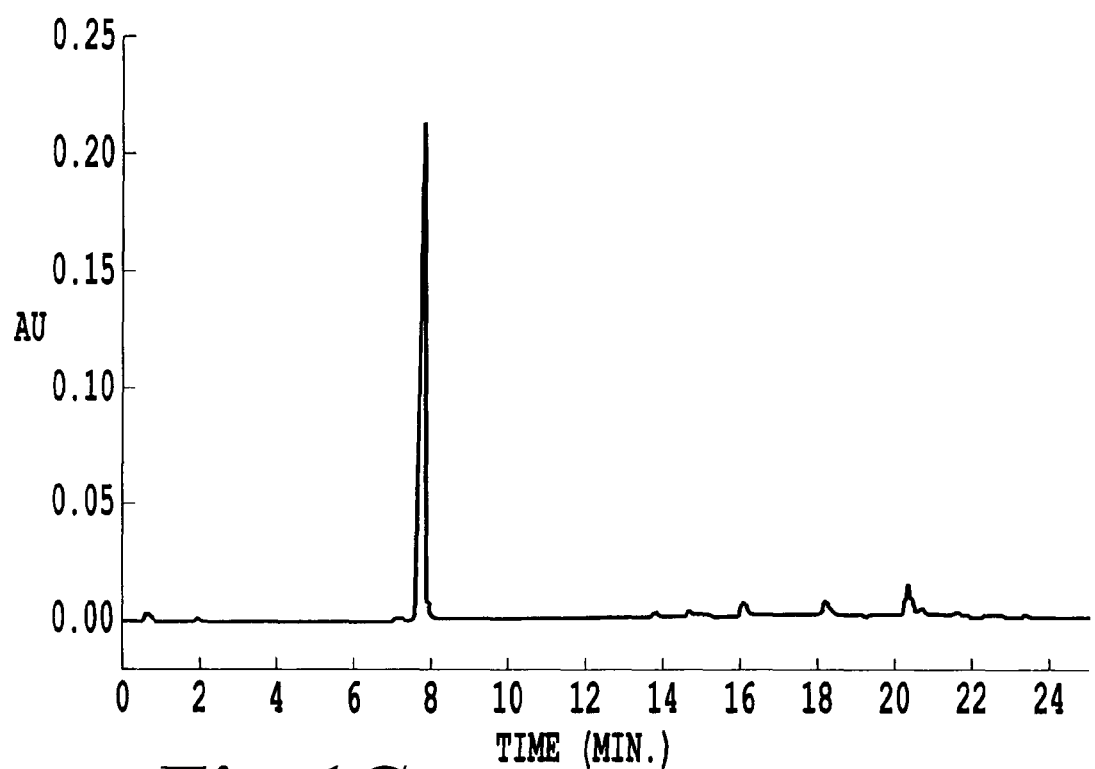

Photolysis rates in solution for some of the preferred protective groups of the invention as compared to the established NPPOC group were measured as described in Example 37, by irradiating solutions of the protected nucleosides at 365 nm with a Hg lamp. The light-induced deprotection was monitored by HPLC at different time intervals. As discussed in detail below the corresponding half-lives of the photocleavage reactions are set forth in Tables 1 and 2. The HPLC chromatograms obtained after the photolysis of 5'-tBuC-NP-POC-dT (25) for 0 sec., 60 sec. and 600 sec. are depicted in FIG. 1 for purposes of illustration.

Table 1 lists the half-lives of various 5'-protected deoxythymidines in aqueous methanolic solutions, as compared to the half-live of the 5'-NPPOC protected deoxythymidine (26). With reference to Table 1, it can be seen that the 2-(5-phenyl-2-nitrophenyl)-1-propyl oxycarbonyl (P—NPPOC) group is removed fastest under these conditions with a half-life of 17 seconds, corresponding to a 3.2-fold increase of the photolysis rate relative to the parent NPPOC-group, as evident from entries 1 and 7. In contrast, the alkoxycarbonyl substituted protective groups of compounds 24 and 25 (entries 5 and 6) were cleaved significantly slower, 77 and 75 seconds respectively, under the same conditions. Furthermore, as evident from entries 1 to 4, the rate of photolysis of the P—NPPOC group is virtually independent of the respective nucleobase employed. All the P—NPPOC protected nucleosides examined, the dT-derivative, as well as, the base-protected dC(tac)-, dA(tac)- and dG(tac)-derivatives, exhibited almost identical $t_{1/2}$-values of 17 to 19 seconds. In a second set of experiments the photolytic rates of these four nucleosides dissolved in aqueous acetonitrile were also determined, resulting in slightly lower $t_{1/2}$-values, again showing no dependency on the nucleobase, as depicted in Table 2. A further analogy to the experiments in aqueous methanolic solution is the 3.9 fold higher $t_{1/2}$-value for the NPPOC-protected deoxythymidine as compared to P—NPPOC-protection, as evident from entries 1 and 5 of Table 2.

Table 3 sets forth the $t_{1/2}$-values for nucleosides derivatized with the Bz-NPPOC protective group and substituted derivatives thereof, which were measured as described in Example 37. These data were acquired in the same manner as the data compiled in Tables 1 and 2, with the exception that solutions of methanol or acetonitrile containing 5% water were employed and an improved optical focusing was used. The latter modification significantly reduces the $t_{1/2}$-values, as indicated by a $t_{1/2}$-value of only 5 seconds for 5'-NPPOC-dT, which is less than the tenth of the previously measured value shown in Table 1. As can be seen in Table 3, entry 1, the $t_{1/2}$-value of 5'-Bz-NPPOC-dT (28) is less than half of that measured for the corresponding NPPOC-derivative (26). Under these conditions, 5'-Bz-NPPOC protected dA(bz) (29) and dC(ac) (30) also have $t_{1/2}$-values in the range of about 2 seconds (entries 2 and 3), in aqueous methanol, as well as, in aqueous acetonitrile. Thus, it can be assumed that as in the case of the P—NPPOC group, the $t_{1/2}$-values of the Bz-NPPOC protective group are also largely independent of the respective nucleobase employed. Table 3 includes the $t_{1/2}$-values for the 5'-Bz-NPPOC-protected dT compounds 31, 32 and 33, in which the benzoyl moiety of the protective group is derivatized with a fluoride at positions 2, 3 and 4, respectively. Again, for these compounds $t_{1/2}$-values of about 2 seconds were observed in both solvent systems, as evident from entries 4 to 6.

Figure 2:
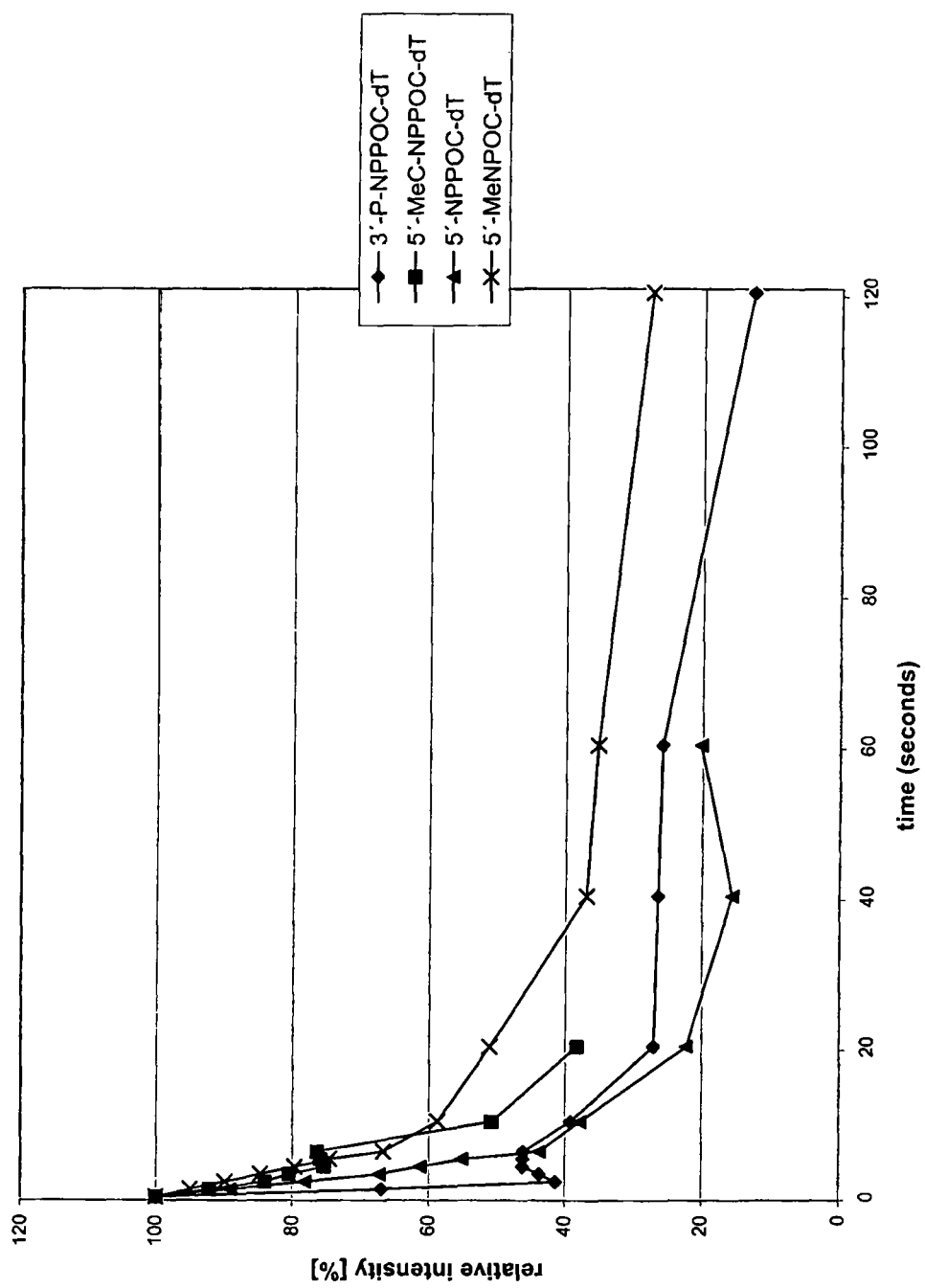
FIG. 2 displays the time dependency of the photolytic decay of deoxythymidines protected by the photosensitive protective groups of the invention and the prior art, respectively, upon irradiation at 365 nm under dry conditions measured as described in Example 38.
Figure 3:
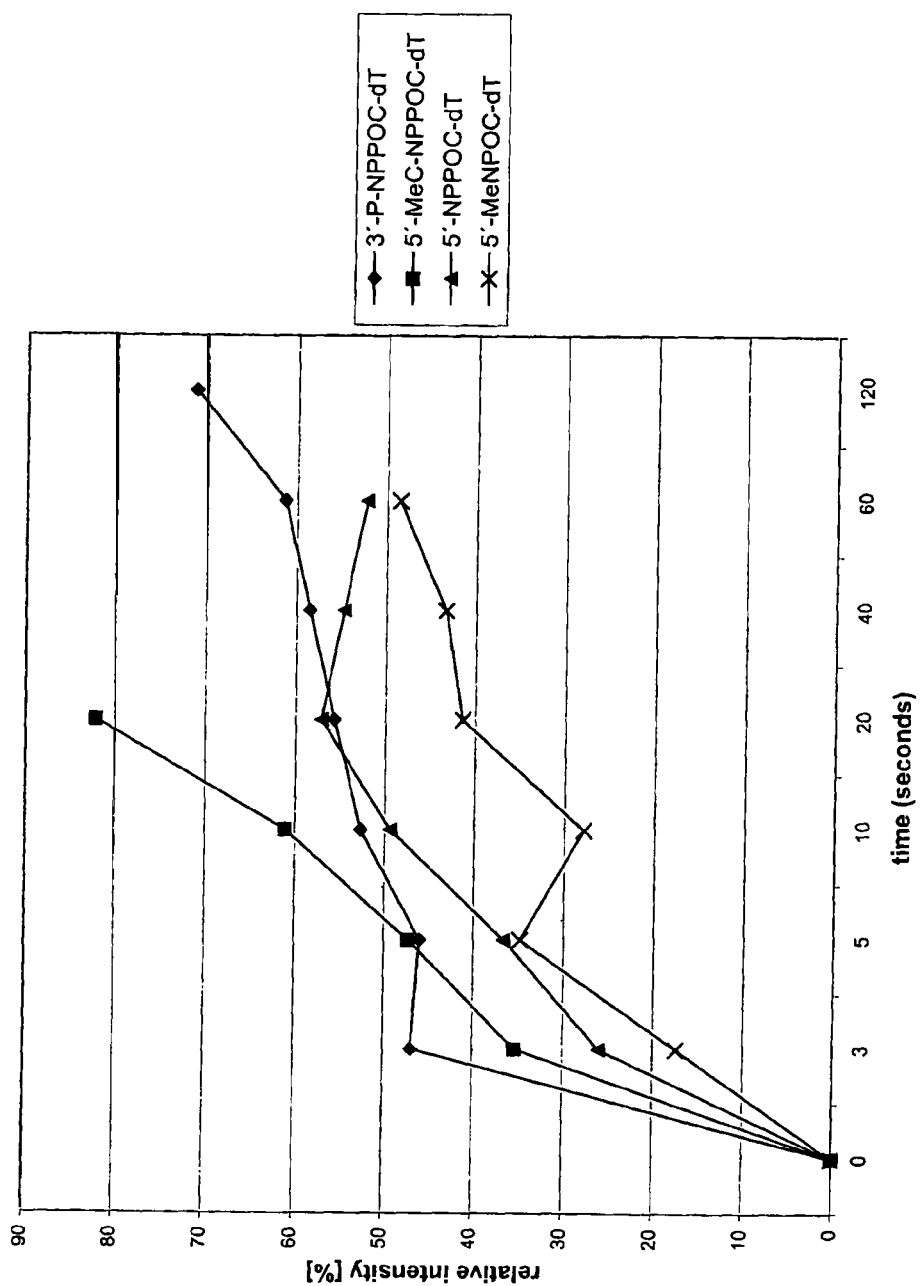
FIG. 3 displays the time dependency of the photolytic release of deoxythymidine from the photosensitively protected deoxythymidines of the invention and the prior art, respectively, upon irradiation at 365 nm under dry conditions, considering a further aspect of the same experiment as analyzed in FIG. 2 and performed according to Example 38.

In the context of the photolithographic fabrication of microarrays with the aforementioned α-methyl-6-nitropiperonyloxycarbonyl (MeNPOC) group, dry deprotection has been reported to be advantageous, particularly with regard to automation capability and deprotection rates, as described by Barone et al., Nucleosides, Nucleotides & Nucleic Acids 20:525-531 (2001), and McGall et al., J. Am. Chem. Soc. 119:5081-5090 (1997). Corresponding experiments under dry-deprotection conditions were carried out employing nucleosides bearing the photolabile protective groups of the invention as described in Example 38. Briefly, the respective nucleosides were irradiated at 365 nm in a dry state on a polystyrene surface and the time dependent deprotection of the educt as well as the formation of the product were quantified by HPLC. The results are set forth in FIGS. 2 and 3. As can be seen in FIG. 2, both 3'-P—NPPOC- and 5'-NPPOC-protected deoxythymidines (27) and (26) were deprotected significantly faster than 5'-MeNPOC-protected deoxythymidine and 5'-MeC-NPPOC-deoxythymidine (24), an example of the alkoxycarbonyl substituted protective groups of the invention. 5'-MeC-NPPOC-deoxythymidine (24), however, provided substantially higher yields of deoxythymidine as compared to all of the other photosensitively protected deoxythymidines investigated in this set of experiments, as apparent from FIG. 3. Thus, the alkoxycarbonyl substituted protective groups of the invention, as exemplified by the methoxy derivative included in compound (24) and the tert-butoxy derivative included in compound (25), have similar photolysis rates, but superior conversion rates as compared to the MeNPOC group, which to date has been considered to give the best overall performance in dry-mode photolysis.

In a separate set of experiments, using the method described in Example 38 including the aforementioned improved optical focusing, the half lives for the photolytic removal of the Bz-NPPOC protective group and some of its fluorinated derivatives were determined. The results are set forth in Table 4. With reference to Table 4 (entries 1 through 6), it can be seen that all of these compounds, with the exception of the (4-fluor-Bz)-NPPOC-protected deoxythymidine (33), exhibited $t_{1/2}$-values of 6.0 seconds. This value is about 3 times higher than the $t_{1/2}$ values of the respective wet deprotections, as compiled in Table 3, but less than half of the $t_{1/2}$-value measured for 5'-NPPOC-dT (26) (Table 4, entry 7). Thus, taking into consideration the results as summarized for FIG. 2, the Bz-NPPOC protective group, as well as, its fluorinated derivatives, exhibit similar or in most cases shorter photolysis rates than all of other photolabile protective groups described herein. With regard to cleavage yield and efficiency these protective groups are even more competitive as demonstrated below.

Also included in this invention is an improved method for the preparation of oligonucleotides on a support by stepwise elongation either in the 3' to 5' direction employing nucleotidic building blocks featuring photocleavable protective groups at their 5'-terminus, or in the 5' to 3' direction employing such building blocks that are accordingly 3'-protected. The latter case is further specified in parentheses below. Said method is comprised of the following steps:

1. attaching a first nucleotide to a support via its 3'(5')-hydroxyl group, the 5'(3')-position of which is derivatized with a photocleavable protective group of the invention;
2. irradiating the support-bound nucleotide resulting from step 1, to remove the photocleavable protective group, thereby deprotecting the 5'(3')-hydroxyl group;
3. contacting the support-bound nucleotide obtained in step 2 in the presence of an activator with a second nucleotide comprising a 5'(3')-protective group of the invention and a 3'(5')-phosphoramidite functional group which reacts with the 5'(3')-hydroxyl group of the support-bound nucleotide forming an internucleosidic phosphorus linkage;
4. optionally capping any unreacted 5'(3')-hydroxyl groups with an inert protective group, to prevent further coupling;
5. oxidizing the newly formed internucleosidic phosphorous linkage to the naturally occurring pentavalent state;
6. optionally repeating steps 2 to 5 while successively applying the nucleoside monomers in a predetermined order until the desired oligonucleotide strand is completed; and
7. removing all nucleobase and phosphate protective groups.

With the exception of the step involving the removal of the photolabile protective group of the invention all other steps are analogous to known methods for solid phase oligonucleotide synthesis and well known to those of skill in the art.

Said general method of the invention for the preparation of oligonucleotides encompasses the fabrication of arrayed assemblies of oligonucleotides, in particular microarrays that are useful for hybridization-based genomic screenings in a parallel fashion. More specifically, such microarrays may be produced by applying photolithographic techniques, e.g. those described by Fodor et al. (1991) Science 251:767-773 (1991), or according to the technique relying on the 'maskless array synthesizer' (MAS) as described by Singh-Gasson et al. (1999) Nature Biotech. 17:974-978 and Nuwaysir et al. (2002) Genome Research 12:1749-1755.

A MAS was employed in experiments described below in order to demonstrate the advantageous properties of the novel photolabile protective groups of the invention, in particular the enhanced cleavage rates and the improved cycle efficiency in the preparation of oligonucleotide microarrays. As explained in detail by Sengh-Gasson et al. (1999) Nature Biotech. 17:974-978, the MAS forms a UV image of the virtual mask on the surface of the glass substrate that serves as solid support on which an array of oligonucleotides is assembled. Prior to being mounted in the MAS's flow cell reaction chamber, which is connected to a standard DNA synthesizer, said glass substrate is covalently modified with a silane reagent as described in Example 39 to provide hydroxyl ethyl groups from which the probe syntheses can be initiated.

Figure 4:
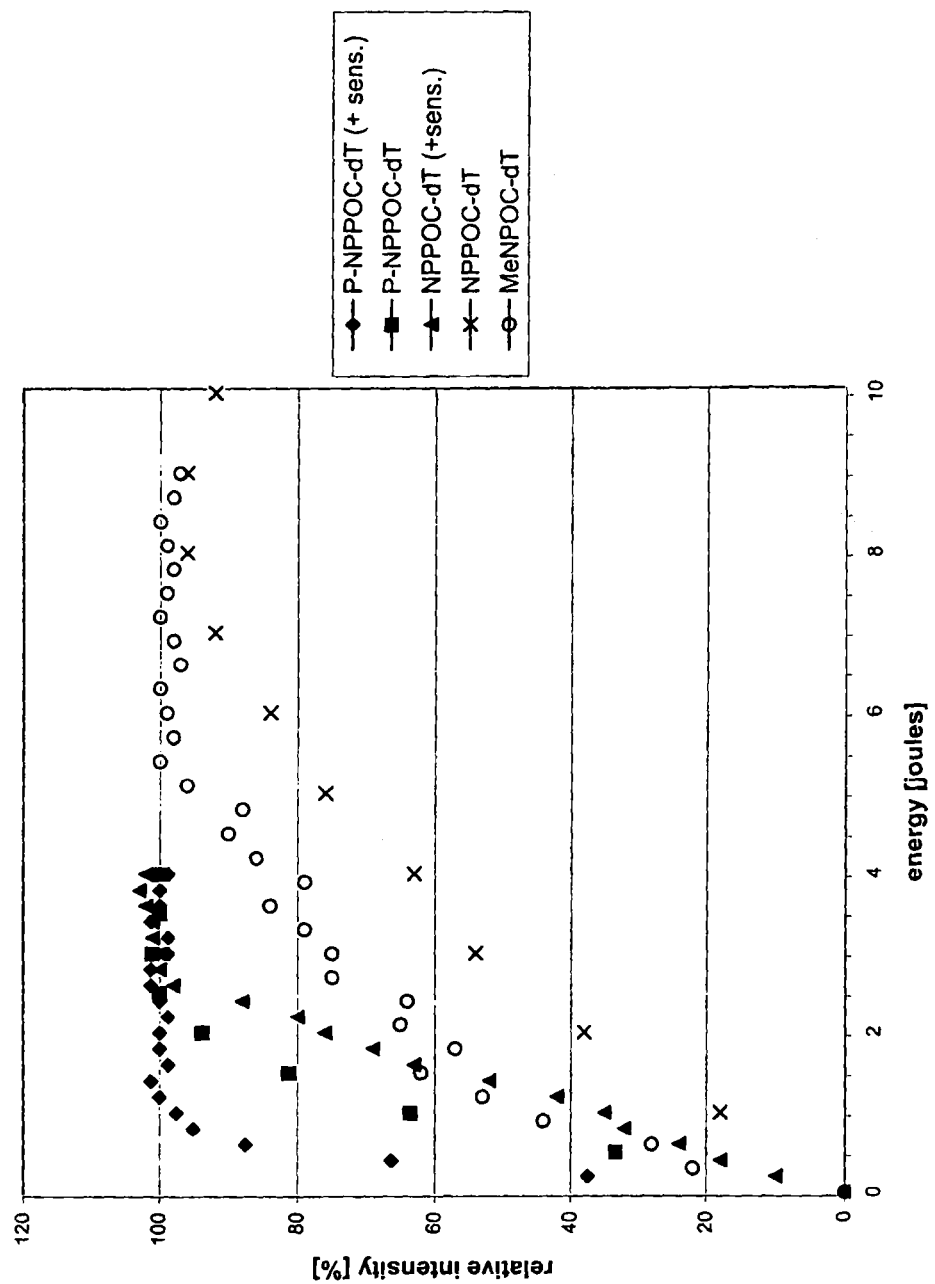
FIG. 4 displays the dependency of the photolytic release of deoxythymidine in solution of support bound deoxythymidines protected by photosensitive protective groups of the invention and the prior art, respectively, on irradiation energy, which is linearly related to illumination time, measured as described in Example 40.

To study the on-chip deprotection of the inventive photolabile protective groups in the presence of a solvent as compared to the well established NPPOC and MeNPOC protective groups, separate arrays for each of these groups were prepared on silanized glass slides, as described in Example 40. Briefly, 5'-protected deoxythymidine 3'-phosphoramidites were coupled to the slides during the first synthetic cycle, followed by illuminating different areas on each slide with varying doses of irradiation. The fluorescent Cy3 phosphoramidite was then attached to the arrays in the next cycle, providing a relative measure for the 5'-hydroxyl groups that were photolytically released. The results are set forth in FIG. 4 which shows that significantly less energy is needed for the P—NPPOC group to reach maximum release in relation to both the MeNPOC and the NPPOC group, corresponding to a reduction of the deprotection time by a factor of >2 and >3, respectively. Analogous to what has been described by Wöll et al., poster presentation on the EuroBiochips 2002, even faster removal of the P—NPPOC group is accomplished when the photosensitizer thioxanthone was present in the deprotection solvent, as can also be seen in FIG. 4.

Figure 5:
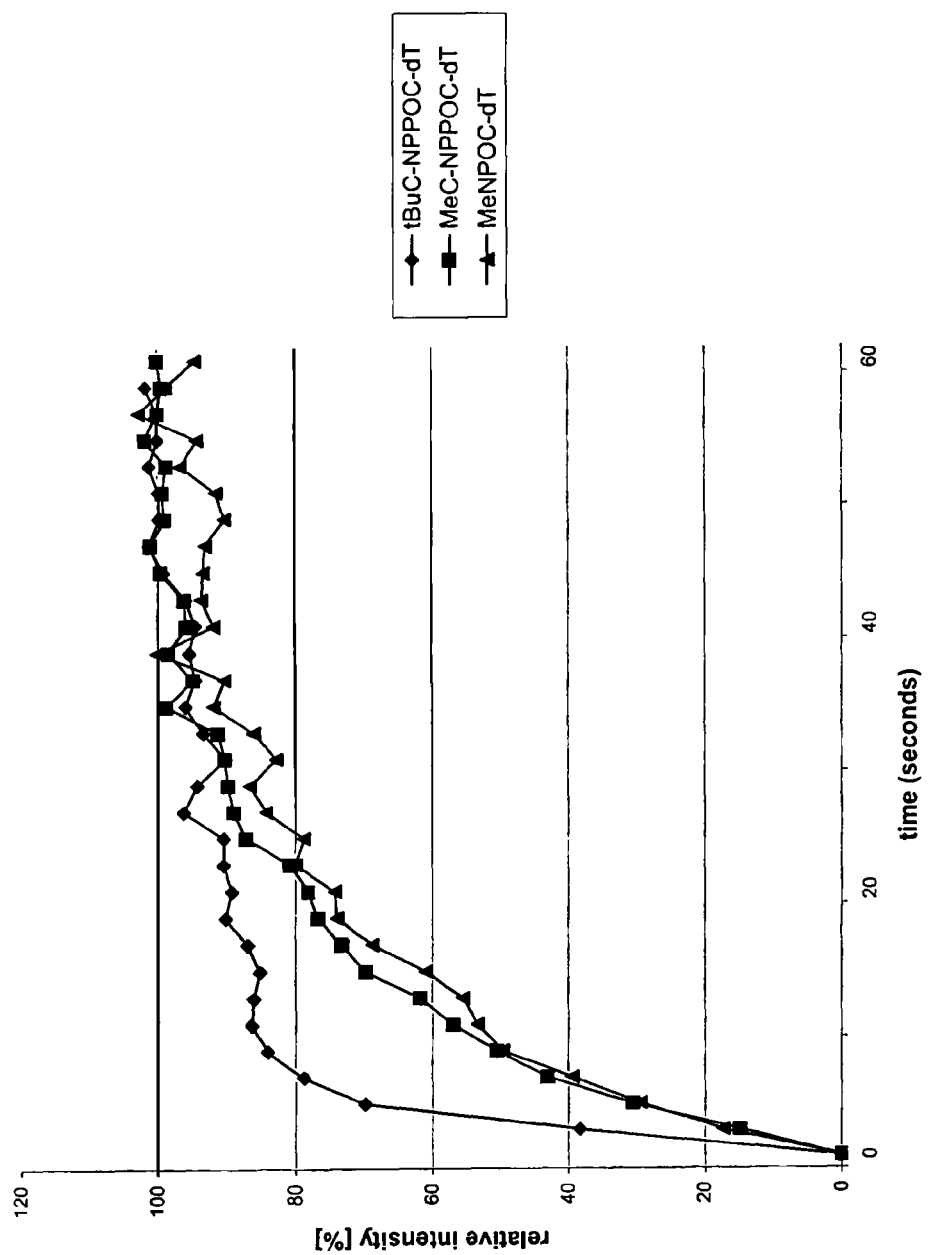
FIG. 5 displays the dependency of the photolytic release of deoxythymidine under dry conditions of support bound deoxythymidines protected by the photosensitive protective groups of the invention and the prior art, respectively, on irradiation energy, which is linearly related to illumination time, measured as described in Example 41.

Similar on-substrate experiments with regard to dry deprotection were performed as described in Example 41, in order to verify the positive results obtained for the alkoxycarbonyl derivatives of the light-sensitive protective groups of the invention. In contrast to the aforementioned MAS based experiments all solvents were removed prior to the deprotection step and the array was dried with an argon stream through the flow cell. As depicted in FIG. 5, the results indicate that the tBuC-NPPOC group is removed significantly faster, and the MeC-NPPOC slightly faster than the MeNPOC group.

Finally, the 5'-Bz-NPPOC-protected deoxythymidine phosphoramidite was employed to build arrays of $dT_{12}$ oligonucleotides as described in Example 42, applying the dry deprotection procedure described in Example 41. In analogy to a procedure described by McGall et al., J. Am. Chem. Soc. 119:5081-5090 (1997), the yield for each cycle of the oligonucleotide synthesis was determined by derivatizing a respective subset of features on the array with Cy3 phosphoramidite following the photolysis step. After completion of the synthesis the cycle yields were derived from the fluorescence emissions of the individual subsets. The results are set forth in Table 5, which shows that even under generic, non-optimized deprotection conditions the assembly of $dT_{12}$ using Bz-NPPOC-protection was accomplished applying distinctly shorter exposure times in identical or higher average cycle yields, compared to the corresponding NPPOC- and MeNPOC-protection schemes.

In conclusion, the superior performance of the photolabile protective groups of the invention is demonstrated for the light-directed preparation of oligonucleotide arrays. With regard to array fabrication comprising deprotection steps that involve irradiation with a solvent present on the support surface, P—NPPOC-protection clearly out performs the commonly used NPPOC-protection in terms of deprotection times and in terms of the quality of the assembled oligonucleotides. With regard to array fabrication that comprises deprotection including irradiation of the dry support surface, MeC-NPPOC-, tBuC-NPPOC- and in particular Bz-NPPOC-protection are superior to MeNPOC-protection in terms of the aforementioned criteria. In addition, the reagents to introduce the Bz-NPPOC protective group are readily accessible by comparably straightforward and high-yielding synthetic routes.

The following examples are provided to explain and illustrate the present invention and are not intended to limit the scope of the invention in any way.

EXAMPLES

Example 1

Preparation of 3-ethyl-4-nitro-halo benzenes (10)
(Scheme 1)

a) 3-Ethyl-acetylamino benzene (8). Compound (8) was prepared according to a modified procedure-originally described by Wieland et al. (1938) Liebigs Ann., 536:89, which is incorporated herein by reference in its entirety. With reference to Scheme 1, 3-ethylaniline (7) (25 mL, 27 g, 0.22 mol) was added to acetic anhydride (100 mL) in an ice bath and the reaction mixture was stirred for 10 minutes with cooling and for an additional 20 minutes without cooling. Evaporation and subsequent distillation (110-114° C./0.05 mbar) yielded 32.1 g (89%) of compound (8) as light yellow crystals. mp 30-32° C. $R_f$=0.42 (hexanes/EtOAc 1:1). $^1$H NMR: (250 MHz, $CDCl_3$) δ 7.60 (s, 1H, NH), 7.34-7.16 (m, 3H, 3×arom. H), 2.59 (q, 2H, $CH_2$), 2.14 (s, 1H, $C(O)CH_3$), 1.18 (t, 3H, $CH_3$). UV ($\lambda_{max}$ [nm] (log ϵ); MeOH): 206 (3.41); 242 (3.10); 280 (1.76).

b) 4-Amino-2-ethyl-nitrobenzene (9). Compound 9 was prepared using a modified procedure originally described by Wieland et al. (1938) Liebigs Ann., 536:89, which is incorporated herein by reference in its entirety. Specifically, 3-ethyl-acetylamino benzene (8) (39 g, 0.24 mol) was added dropwise to concentrated sulfuric acid (100 mL) with mechanical stirring and ice cooling at a rate such that the temperature did not exceed 25° C. After cooling to −15° C., concentrated nitric acid (9.8 mL, 15 g, 0.24 mol) was added dropwise over 30 minutes under ice cooling at a rate such that the temperature did not exceed −15° C. After 90 minutes, the reaction mixture was poured onto ice and extracted with diethyl ether (3×300 mL). The combined organic phases were washed with water and neutralized with solid sodium bicarbonate. After drying and evaporation in vacuo, the deep red oil obtained (51 g) was heated with concentrated HCl (175 mL) for 2.5 hours under reflux. After cooling, the precipitate was filtered off, dispersed in 1 N NaOH (400 mL) and extracted with diethyl ether (3×250 mL). The combined organic phases were dried, evaporated and further purified by silica column chromatography (hexanes/EtOAc 8:1 and 4:1). The product, compound (9) was obtained in 56% yield (22.1 g) as yellowish crystals. mp 84-85° C. $R_f$=0.27 (silica, hexanes/EtOAc 7:3). $^1$H NMR: (250 MHz, $CDCl_3$) δ 7.96 (m, 1H, H(6)), 6.47 (m, 2H, H(5), H(3)), 4.23 (s, 2H, $NH_2$), 2.93 (q, 2H, $CH_2$), 1.24 (t, 3H, $CH_3$). UV ($\lambda_{max}$ [nm] (log ϵ); MeOH): 203 (4.21), 231 (3.82), [245 (3.69)], [372 (4.09)].

c) 3-Ethyl-4-nitro-bromobenzene (10b). To a mixture of HBr (48%, 95 mL) and water (155 mL), preheated to 60° C. was added 4-amino-2-ethyl-nitrobenzene (9) (16.6 g, 0.1 mol) and the mixture was cooled rapidly in an ice bath. At a temperature below 5° C., sodium nitrite (7.59 g, 0.11 mol) in water (20 mL) was added drop wise and after 10 minutes a spatula of urea was added and the reaction stirred for 5 more minutes under ice cooling. The precipitate was filtered by suction and added to a mixture of copper sulfate pentahydrate (15 g, 60 mmol) and copper powder (6 g, 94 mmol) in HBr (48%, 63 mL) and water (37 mL) after which the mixture was heated to 80° C. for a period of 70 minutes. After cooling the mixture was extracted with ethyl acetate (4×150 mL) and the combined organic extracts were washed with 1 N NaOH (200 mL) and water, dried and evaporated. Distillation afforded 18.53 g (80%) of 3-ethyl-4-nitro-bromobenzene (10b) as a yellow oil. bp 75-83° C./0.007 mbar. $R_f$=0.76 (hexanes/EtOAc 4:1). $^1$H NMR δ (250 MHz, $CDCl_3$): 7.76 (d, 1H, H(6)), 7.50 (d, 1H, H(3)), 7.45 (dd, 1H, H(5)), 2.89 (q, 2H, $CH_2$), 1.27 (t, 3H, $CH_3$). UV ($\lambda_{max}$ [nm] (log ϵ); MeOH): 203 (4.19), [217 (3.98)], 267 (3.91), [320 (3.21)]. Elemental analysis for $C_8H_8BrNO_2$ (230.07 g/mol): calc.: C, 41.77; H, 3.50; N, 6.09. found: C, 41.71; H, 3.59; N, 6.08.

d) 3-Ethyl-4-nitro-chlorobenzene (10a). Compound 10a was obtained in a yield of 46% as a yellow oil, according to the method described above substituting with concentrated HCl and copper (I) chloride. $^1$H NMR (250 MHz, $CDCl_3$) δ 7.85 (m, 1H, H(6)), 7.34 (m, 1H, H(3)), 7.29 (dd, 1H, H(5)), 2.90 (q, 2H, $CH_2$), 1.24 (t, 3H, $CH_3$). UV ($\lambda_{max}$ [nm] (log ϵ); MeOH): 206 (4.09), [216 (3.91)], 263 (3.79)], [334 (2.84)]. Elemental analysis for $C_8H_8ClNO_2$ (185.61): calc.: C, 51.77; H, 4.34; N, 7.55. found: C, 51.65; H, 4.34; N, 7.63.

e) 3-Ethyl-4-nitro-iodobenzene (10c). Compound 10c was obtained according to the method described above substituting with dilute $H_2SO_4$ and sodium iodide in a yield of 57% as red oil. $^1$H NMR (250 MHz, $CDCl_3$) δ 7.72 (m, 1H, H(3)), 7.66 (dd, 1H, H(5)), 7.58 (d, 1H, H(6)), 2.85 (q, 2H, $CH_2$), 1.25 (t, 3H, $CH_3$). UV ($\lambda_{max}$ [nm] (log ϵ); MeOH): 203 (4.22), [220 (3.88)], 281 (3.87)], [328 (3.22)]. Elemental analysis for $C_8H_8INO_2$ (277.06): calc.: C, 34.68; H, 2.91; N, 5.06. found: C, 34.84; H, 2.92; N, 4.90.

Example 2

Preparation of 3-ethyl-4-nitrobiphenyl (11a)
(Scheme 2)

To a solution of 3-ethyl-4-nitro-bromobenzene (10b) (6.9 g, 26 mmol) in toluene (40 mL) was added ethanol (10.5 mL), an aqueous solution of sodium bicarbonate (2 M, 16 mL), benzene boronic acid (3.82 g, 31 mmol) and tetrakis(triphenylphosphine)-palladium (0) (400 mg, 0.35 mmol) and the mixture heated to reflux for 5 hours. After cooling saturated aqueous NaCl solution (30 mL) was added, the mixture was extracted with ethyl acetate (2×25 mL) and the combined organic extracts were dried and evaporated. After silica column chromatography (hexanes and hexanes/EtOAc 9:1), compound 11a was obtained in 92% yield (5.43 g) as yellow crystals. mp 54-56° C. $R_f$=0.67 (hexanes/EA 9:1). $^1$H NMR (250 MHz, CDCl$_3$) δ 7.99 (d, 1H, arom. H), 7.61 and 7.38 (m, 7H, 7 arom. H), 2.99 (q, 2H, CH$_2$), 1.33 (t, 3H, CH$_3$). UV ($\lambda_{max}$ [nm] (log ε); MeOH): 205 (4.52), [225 (4.05)], 291 (4.04). Elemental analysis for C$_{14}$H$_{13}$NO$_2$ (227.26): calc.: C, 73.99; H, 5.75; N, 6.16. found: C, 73.84; H, 5.68; N, 5.81.

Example 3

Preparation of 3-ethyl-4-nitro-4'-methoxybiphenyl (11b) (Scheme 2)

3-Ethyl-4-nitro-4'-methoxybiphenyl (11b) was synthesized as described in Example 2, using 4-methoxybenzene boronic acid as the reagent. Following purification compound 11b was obtained in 93% yield as yellow crystals. mp 94-95° C. $^1$H NMR (250 MHz, CDCl$_3$) δ 7.97 (d, 1H, 1 arom. H), 7.51 (m, 4H, 4 arom. H), 6.70 (dd, 2H, 2 arom. H) 3.85 (s, 3H, OMe), 2.99 (q, 2H, CH$_2$), 1.32 (t, 3H, CH$_3$). UV ($\lambda_{max}$ [nm] (log ε); MeOH): 204 (4.52), 232 (4.13), 320 (4.07)]. Elemental analysis for C$_{15}$H$_{15}$NO$_3$ (257.29): calc.: C, 70.02; H, 5.88; N, 5.44. found: C, 70.00; H, 5.97; N, 5.14.

Example 4

Preparation of 2-(3-ethyl-4-nitrophenyl) naphthalene (11c) (Scheme 2)

2-(3-Ethyl-4-nitrophenyl) naphthalene (11c) was synthesized as described in Example 2, using 2-naphthyl boronic acid as the reagent. Compound 11c was obtained in 93% yield as yellow crystals. mp 110-111° C. $^1$H-NMR (250 MHz, CDCl$_3$) δ 8.03 (m, 2H, 2 arom. H), 7.90 (m, 3H, 3 arom. H), 7.66 (m, 3H, 3 arom. H), 7.52 (m, 2H, 2 arom. H), 3.03 (q, 2H, CH$_2$), 1.36 (t, 3H, CH$_3$). UV ($\lambda_{max}$ [nm] (log ε); MeOH): 212 (4.61), 233 (4.59), [271 (4.15)], 310 (4.14), [339 (3.96)]. Elemental analysis for C$_{18}$H$_{15}$NO$_2$ (277.32): calc.: C, 77.96; H, 5.45; N, 5.05. found: C, 77.79; H, 5.25; N, 4.76.

Example 5

Preparation of 4-ethyl-3-nitrobenzoic acid methyl ester (11d) (Scheme 3)

a) 4-Ethyl-3-nitrobenzoic acid (13) (Scheme 3), was prepared from 4-ethylbenzoic acid (12) according to a procedure described by Fahim et al. (1952) J. Chem. Soc. 4519-4521, which is incorporated herein by reference in its entirety. The product was obtained as a colourless solid in 95% yield. mp 157-159° C. $R_f$=0.11 (hexanes/EA 1:1). $^1$H NMR (250 MHz, DMSO-d$_6$) δ 8.33 (d, 1H, arom. H(2)), 8.12 (dd, 1H, arom. H(6)), 7.65 (d, 1H, arom. H(5)), 2.86 (q, 2H, CH$_2$CH$_3$), 1.20 (t, 3H, CH$_2$CH$_3$).

b) 4-Ethyl-3-nitrobenzoic acid methyl ester (11d). To a solution of 4-ethyl-3-nitrobenzoic acid (13) (9.76 g, 50 mmol) in 40 mL dry methanol was added conc. H$_2$SO$_4$ (1.5 mL) and the mixture was heated under reflux for 3 hours. After cooling to room temperature, the reaction mixture was suspended in CH$_2$Cl$_2$ (50 mL) and extracted with a saturated solution of NaHCO$_3$ (50 mL). The aqueous phase was re-extracted twice with CH$_2$Cl$_2$ (50 mL) and the combined organic extracts were dried over Na$_2$SO$_4$ and evaporated. The raw product (10.24 g, 49 mmol, 98%) was used without further purification. $R_f$=0.59 (hexanes/EA 9:1). $^1$H NMR (250 MHz, CDCl$_3$) δ 8.48 (d, 1H, arom. H(2)), 8.15 (dd, 1H, arom. H(6)), 7.44 (d, 1H, arom. H(5)), 3.93 (s, 3H, COOCH$_3$), 2.93 (q, 2H, CH$_2$CH$_3$), 1.28 (t, 3H, CH$_2$CH$_3$).

Example 6

Preparation of 4-ethyl-3-nitrobenzoic acid tert-butyl ester (11e) (Scheme 3)

A solution of 4-ethyl-3-nitrobenzoic acid (13) (9.76 g, 50 mmol), N,N-di-cyclohexylcarbodiimide (11.35 g, 55 mmol), tert-butanol (4.8 g, 65 mmol) and 4-pyrrolidinopyridine (740 mg, 5 mmol) in dry CH$_2$Cl$_2$ (150 mL) was stirred for 3 hours at room temperature, filtered, and the filtrate was evaporated to dryness. The raw material (15.09 g) was absorbed onto silica gel (20 g) and was then purified via flash chromatography (120 g silica, column: 5×14 cm, solvent: hexane/ETOAC, applying the following step gradient: 600 mL hexane, 600 mL 20:1 (v/v), 330 mL 10:1 (v/v) and 270 mL 8:1 (v/v)). Compound 11e (10.67 g, 42 mmol, 89% yield) was obtained as a bright yellow oil. $R_f$=0.59 (hexane/EtOAc 9:1). $^1$H NMR (250 MHz, CDCl$_3$) δ 8.38 (d, 1H, arom. H(2)), 8.07 (dd, 1H, arom. H(6)), 7.39 (d, 1H, arom. H(5)), 2.90 (q, 2H, CH$_2$CH$_3$), 1.56 (s, 9H, 3×CH$_3$ COOtBu), 1.21 (t, 3H, CH$_2$CH$_3$).

Example 7

Preparation of 4-α-cyanobenzylidene-6-ethyl-2,5-cyclohexadien-1-one oxime (16) (Scheme 4)

To a solution of potassium hydroxide (240 g, 4.28 mol) in methanol (1000 mL) was added phenylacetonitrile (14) (120 mL, 121.8 g, 1.04 mol) and 1-ethyl-2-nitrobenzene (15) (120 mL, 134.5 g, 0.89 mol). The mixture was stirred at 50-60° C. for 5 hours, cooled in an ice bath and diluted with water (1600 mL). A solution of acetic acid (440 mL) in water (400 mL) was then added drop wise to the ice cooled reaction mixture. The resulting suspension was stirred overnight in an ice bath. The precipitate was filtered off, air-dried for several days and washed with hexane to provide 200 g (0.80 mol, 90%) of compound 16 as a yellow powder.

Example 8

Preparation of 3-ethyl-4-nitro-benzophenone (11f)

A mixture of the oxime 16 (200 g, 0.80 mol), potassium hydroxide (188 g, 3.36 mol), methanol (190 mL) and water (1900 mL) was heated to 70-90° C. Under vigorous stirring an aqueous solution of hydrogen peroxide (35%, 1400 mL) was added drop wise to the hot reaction mixture over a period of approximately 6 to 8 hours. The mixture was then refluxed over night, cooled to ambient temperature and the oily precipitate was allowed to settle down. The aqueous phase was separated and extracted with ethyl acetate (1000 mL). The organic phase obtained and the oily precipitate were combined, diluted with some toluene and concentrated in vacuo. The residue was dissolved in CH$_2$Cl$_2$, filtered over silica gel (380 g), evaporated in vacuo, crystallized from methanol and air dried to give 58.5 g (0.23 mol, 29%) of compound 11f as yellow crystals.

Example 9

General Protocol for the Preparation of 2-(5-aryl-2-nitrophenyl)propanol derivatives (Scheme 5)

The respective ethylbenzene derivative (11) (5 mmol) was treated with para formaldehyde (5 mmol) in dry DMSO (10 mL) and potassium tert-butoxide (0.05-0.5 mmol) in tert-butanol (3 mL). After 15 minutes of stirring at room temperature and heating for 2 hours at 80° C., the mixture was cooled to room temperature. The reaction mixture was then neutralized with conc. HCl, diluted with a saturated aqueous solution of NaCl (25 mL) and extracted with ethyl acetate (3×20 mL). The combined organic extracts were then dried and evaporated. Silica column chromatography afforded the desired product.

Example 10

Preparation of 2-(5-phenyl-2-nitrophenyl)propanol (4a)

Compound 4a was prepared according to the general method described in Example 9 starting with from 3-ethyl-4-nitrobiphenyl (11a) to obtain compound 4a as a yellow oil in 68% yield. $^1$H NMR (250 MHz, CDCl$_3$) δ 7.85 (d, 1 arom. H), 7.65 (d, 1 arom. H), 7.59-7.38 (m, 6 arom. H), 3.83 (m, 2H, CH$_2$), 3.62 (m, 1H, OH), 1.73 (br. s, 1H, OH), 1.37 (d, 3H, CH$_3$). UV ($\lambda_{max}$ [nm] (log ε); MeOH): 204 (4.53), [231 (4.03)], 281 (3.94)], 336 (3.70). Elemental analysis for C$_{14}$H$_{13}$NO$_2$ (227.26): calc.: C, 70.02; H, 5.88; N, 5.44. found: C, 69.67; H, 5.73; N, 5.30.

Example 11

Preparation of 2-[5-(4-methoxyphenyl)-2-nitrophenyl]propanol (4b)

Compound 4b was prepared according to the general method described in Example 9 starting from 3-ethyl-4-nitro-4'-methoxybiphenyl (11b) to obtain compound 4b as yellow crystals in 57% yield. $^1$H NMR (250 MHz, CDCl$_3$) δ 7.84 (d, 1 arom. H), 7.53 (dm, 4 arom. H), 6.99 (dd, 2 arom. H), 3.83 (m, 5H, OMe and α-CH$_2$), 3.66 (m, 1H, β-CH), 1.60 (br. s, 1H, OH), 1.36 (d, 3H, CH$_3$). UV ($\lambda_{max}$ [nm] (log ε); MeOH): 204 (4.56), 232 (4.13), 305 (4.01). Elemental analysis for C$_{16}$H$_{17}$NO$_4$ (287.31): calc.: C, 66.89; H, 5.96; N, 4.88. found: C, 66.78; H, 5.83; N, 4.77.

Example 12

Preparation of 2-[5-(2-naphthyl)-2-nitrophenyl]propanol (4c)

Compound 4c was prepared according to the general method described in Example 9 starting from 2-(3-ethyl-4-nitrophenyl) naphthalene (11c) to obtain compound 4c as yellow crystals in 69% yield. mp 118-119° C. $^1$H NMR (250 MHz, CDCl$_3$) δ 8.04 (s, 1 arom. H), 7.91 (m, 3 arom. H), 7.78 (d, 1 arom. H), 7.68 (m, 2 arom. H), 7.52 (m, 2 arom. H), 3.88 (m, 2H, α-CH$_2$), 3.67 (m, 1H, β-CH); 1.78 (br. s, 1H, OH); 1.41 (d, 3H, CH$_3$). UV ($\lambda_{max}$ [nm] (log ε); MeOH): 212 (4.61), 235 (4.57), [274 (4.14)], [303 (4.09)], [340 (3.85)]. Elemental analysis for C$_{19}$H$_{17}$NO$_3$ (307.35): calc.: C, 74.25; H, 5.58; N, 4.56. found: C, 74.22; H, 5.47; N, 4.35.

Example 13

Preparation of 2-(4-methoxycarbonyl-2-nitrophenyl)propanol (4d)

To a suspension of 4-ethyl-3-nitrobenzoic acid methyl ester (11d) (10 g, 48 mmol) and paraformaldehyde (1.8 g, 60 mmol) in DMSO (10 mL) was added in portions potassium tert-butoxide (1.46 g, 12 mmol), during which the colour of the reaction mixture was changing from yellow to purple. After stirring for 2.5 hours at room temperature, the reaction mixture was directly applied to the silica gel bed of a chromatography column (100 g silica, 3.5×14 cm) and eluted with hexane/ethyl acetate (EA) (3:1, v/v). The slightly yellow product (4d) was obtained in 38% yield (4.42 g, 18 mmol). R$_f$=0.24 (hexanes/EtOAc 7:3). $^1$H NMR (250 MHz, CDCl$_3$) δ 8.36 (d, 1H, arom. H(3)), 8.18 (dd, 1H, arom. H(5)), 7.58 (d, 1H, arom. H(6)), 3.93 (s, 3H, COOCH$_3$), 3.78 (m, 2H, α-CH$_2$), 3.54 (sextet, 1H, β-CH), 1.69 (d, 3H, CH$_3$).

Example 14

Preparation of 2-(4-tert-butoxycarbonyl-2-nitrophenyl)propanol (4e)

To a suspension of 4-ethyl-3-nitrobenzoic acid tert-butyl ester (11e) (10 g, 40 mmol) and paraformaldehyde (1.8 g, 60 mmol) in DMSO (10 mL) was added in portions potassium tert-butoxide (590 mg, 5.8 mmol), during which the colour of the reaction mixture was changing from yellow to purple. After stirring for 1 hour at room temperature, the reaction mixture was suspended in CH$_2$Cl$_2$, adsorbed onto silica gel (15 g) in vacuo and purified by flash chromatography (100 g silica, column: 3.5×14 cm, solvent: hexane/EA 3:1). The product was obtained as a yellow oil in 94% yield (10.57 g, 38 mmol). R$_f$=0.34 (hexane/EtOAc 3:1). $^1$H NMR (250 MHz, CDCl$_3$) δ 8.27 (d, 1H, arom. H(3)), 7.58 (dd, 1H, arom. H(5)), 7.53 (d, 1H, arom. H(6)), 3.76 (m, 2H, α-CH$_2$), 3.50 (sextet, 1H, β-CH), 1.81 (t, 1H, OH), 1.57 (s, 9H, 3×CH$_3$ COOtBu), 1.31 (d, 3H, CH$_3$).

Example 15

Preparation of 2-(3-ethyl-4-nitrophenyl)-2-phenyl-1, 3-dioxane (17)

A suspension of 3-ethyl-4-nitro-benzophenone (11f) (20.0 g, 78.4 mmol), 1,3-propandiol (7.15 g, 94.0 mmol), p-toluenesulfonic acid monohydrate (50 mg) in toluene (300 mL) was refluxed using a Dean-Stark-trap for 24 hours. The Dean-Stark-trap was then replaced by a Soxhlet-extractor filled with molecular sieve and the mixture was refluxed for an additional 48 hours to achieve complete conversion. The reaction mixture was then cooled to ambient temperature, washed with an aqueous, saturated solution of NaHCO$_3$ and concentrated in vacuo until crystallization started. The suspension was cooled for 0.5 hours in an ice bath and after which the crystalline product was filtered, washed with a small volume of hexane and air dried to give 22.48 g (72 mmol, 91.5%) compound 17 as yellow crystals.

Example 16

Preparation of 2-(3-(2-hydroxy-1-methylethyl)-4-nitrophenyl)-2-phenyl-1,3-dioxane (18)

A suspension of 2-(3-ethyl-4-nitrophenyl)-2-phenyl-1,3-dioxane (17) (20.0 g, 63.8 mmol), paraformaldehyde (6.5 g, 72.6 mmol) and a methanolic solution of Triton B (35%, 17 mL) in DMSO (100 mL) was stirred for 2 hours at 85° C. The reaction mixture was then cooled to ambient temperature, diluted with CH$_2$Cl$_2$ (200 mL), washed with water (2×200 mL), partially concentrated in vacuo (for azeotropic drying) and filtered over silica gel (35 g). The filtrate was then evaporated in vacuo to give 24.15 g (approx. 70.3 mmol, 110%) of the crude product as a yellow oil.

Example 17

Preparation of 2-(5-benzoyl-2-nitrophenyl)-1-propanol (4f)

To a solution of 2-(3-(2-hydroxy-1-methylethyl)-4-nitrophenyl)-2-phenyl-1,3-dioxane (18) (23.6 g; approx. 69 mmol) in ethanol (350 mL) was added water (70 mL) under vigorous stirring. Concentrated hydrochloric acid (about 12 N aqueous solution, 35 mL) was then added drop wise. The reaction mixture was stirred at ambient temperature for 4 hours, diluted with water and extracted with ethyl acetate. The organic phase was successively washed with an aqueous, saturated solution of NaHCO$_3$ and with water. The organic phase was then concentrated in vacuo and seeded with crystals of the product 4f to provide a yellow solid. Finally, the powdered solid was washed with hexane and air dried to yield 17.83 g (62.5 mmol, 91%) of a yellow powder. $^1$H NMR (250 MHz, DMSO-d$_6$) δ 7.91-7.52 (m, 8H, arom.), 4.75 (br. s., 1H, OH), 3.53 (d, 2H, α-CH$_2$), 3.23 (sextet, 1H, β-CH), 1.24 (d, 3H, γ-CH$_3$).

Example 18

General Protocol for the Preparation of 2-(2-nitrophenyl)-1-propyl oxycarbonylchloride derivatives of Compounds (4a to 4e)

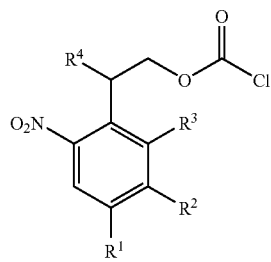

19

To a solution of trichloromethyl chloroformate (2.37 g, 1.4 mL, 12 mmol, 1.2 equivalents) in dry tetrahydrofuran (10 mL), which has been pre-cooled to 0° C., was added over 5 minutes a solution of the respective 2-(2-nitrophenyl)-1-propanol derivative (10 mmol) and triethylamine (1 g, 10 mmol) in tetrahydrofuran (10 mL) with continued cooling. After stirring for 1 hour in an ice bath the reaction mixture was filtered, the filter cake was washed with a little tetrahydrofuran and the combined organic phases were evaporated in vacuo.

Example 19

Preparation 2-(5-phenyl-2-nitrophenyl)-1-propyl oxycarbonylchloride (19a)

Prepared according to the general method described in Example 18, starting from 2-(5-phenyl-2-nitrophenyl)-1-propanol (4a) to obtain a dark yellow oil (3.08 g, 96%), which after drying for 2 hours at 0.1 mbar was used in the next step without further purification. R$_f$=0.91 (CH$_2$Cl$_2$). $^1$H NMR (250 MHz, CDCl$_3$) δ 7.93 (d, 1 arom. H), 7.62-7.40 (m, 7 arom. H), 4.54 (d, 2H, CH$_2$), 3.90 (sextet, 1H, CH), 1.45 (d, 3H, CH$_3$).

Example 20

Preparation of 2-(4-methoxycarbonyl-2-nitrophenyl)-1-propyl oxycarbonylchloride (19d)

Prepared using the general method of Example 18, starting with 2-(4-tert-methoxycarbonyl-2-nitrophenyl)-1-propanol (4d) (1.85 g, 7.7 mmol) to obtain the product in 93% yield (2.16 g, 7.02 mmol) as a yellow oil, which was used in the next step without further purification. R$_f$=0.80 (CH$_2$Cl$_2$). $^1$H NMR (250 MHz, CDCl$_3$) δ 8.45 (d, 1H, arom. H(3)), 8.22 (dd, 1H, arom. H(5)), 7.55 (d, 1H, arom. H(6)), 4.48 (dd, 2H, α-CH$_2$), 3.95 (s, 3H, COOCH$_3$), 3.82 (sextet, 1H, β-CH), 1.41 (d, 3H, CH$_3$).

Example 21

Preparation of 2-(4-tert-butoxycarbonyl-2-nitrophenyl)-1-propyl oxycarbonylchloride (19e)

Prepared starting from 2-(4-tert-butoxycarbonyl-2-nitrophenyl)-1-propanol (4e) (7.05 g, 25 mmol) according to the general procedure described in Example 18. The product, compound 19e was obtained in 97% yield (8.37 g, 24 mmol) as a yellow oil, which was used in the next step without further purification. R$_f$=0.86 (CH$_2$Cl$_2$). $^1$H NMR (250 MHz, CDCl$_3$) δ 8.36 (d, 1H, arom. H(3)), 8.16 (dd, 1H, arom. H(5)), 7.52 (d, 1H, arom. H(6)), 4.48 (m, 2H, α-CH$_2$), 3.76 (sextet, 1H, β-CH), 1.59 (s, 9H, 3×CH$_3$ COOtBu), 1.39 (m, 3H, CH$_3$).

All of the other substituted propanols described above may be treated in the same way to afford the respective chlorocarbonates in excellent yields and sufficient purities.

Example 22

Preparation of 2-(5-benzoyl-2-nitrophenyl)-1-propyl oxycarbonylchloride (19f)

To a solution of trichloromethyl chloroformate (15.83 g, 80 mmol, 0.8 equivalents) in dry tetrahydrofuran (150 mL), which has been pre-cooled to 0° C., was added over a period of approximately 2 hours a solution of 2-(5-benzoyl-2-nitrophenyl)-1-propanol (41) (28.53 g, 100 mmol) and triethylamine (10.12 g, 100 mmol) in tetrahydrofuran (250 mL) with continued cooling. After stirring for 1 hour at ambient temperature the resulting suspension was filtered, the filter cake was washed with a little tetrahydrofuran, and the combined organic phases were concentrated in vacuo to give 19f as yellow oil.

All of the other substituted propanols described above may be treated in the same way to afford the respective chlorocarbonates in excellent yields and sufficient purities.

Example 23

General Protocol for the Introduction of the Photolabile Protective Groups at the 5'-position of 2'-deoxynucleosides The respective 2'-deoxynucleoside (1 mmol) was dried by coevaporation with abs. pyridine (3×3 mL), dissolved in abs.

pyridine (3 mL) and cooled to −50° C. The respective chlorocarbonate (1.35 equivalents for 2'-deoxythymidine, 2'-deoxyadenosine and 2'-deoxyguanosine, or 1.5 equivalents for 2'-deoxycytidine) in abs. $CH_2Cl_2$ (3 mL) was added drop wise over a period of 10 minutes. After 5 hours stirring at −50° C. to −30° C., the reaction mixture was treated with water (10 mL) and the aqueous phase extracted with $CH_2Cl_2$ (3×10 mL). The combined organic phase was dried and coevaporated with toluene (3×10 mL) and purified by silica column chromatography ($CH_2Cl_2$/MeOH 100:1, 100:2, 100:3, 100:3.5 and 100:4). Products were obtained as amorphous solids in moderate to good yields.

Example 24

Preparation of 5'-O-[2-(5-phenyl-2-nitrophenyl)-1-propyl oxycarbonyl]2'-deoxythymidine (20) (Table 1)

Compound 20 was prepared according to the general method described in Example 23 using 2-(5-phenyl-2-nitrophenyl)-1-propyl oxycarbonylchloride (19a), to obtain a yellowish powder in 78% yield. $^1$H NMR (250 MHz, $CDCl_3$) δ 8.91 (br. s, NH), 7.86 (d, 1 arom. H), 7.61-7.38 (m, 7 arom. H), 7.28 (s, 1H, H—C(6)), 6.30 (t, 1H, HC(1')), 4.52-4.21 (m, 5H, $CH_2$, H—C(5'), H—C(3')), 4.09 (m, 1H, H—C(4')), 3.89 (m, 1H, CH), 3.65 (br. s, 1H, HO-(3')), 2.32 (m, 1H, H—C(2')), 2.10 (m, 1H, H—C(2')), 1.76 (d, 3H, $CH_3$-(thy)), 1.41 (d, 3H, $CH_3$). UV ($\lambda_{max}$ [nm] (log ϵ); MeOH): 203 (4.69), 263 (4.25)], [295 (3.95)]; 335 (3.80). Elemental analysis for $C_{26}H_{27}N_3O_9 \times 0.5H_2O$ (534.52): calc.: C, 58.42; H, 5.28; N, 7.86. found: C, 58.82; H, 5.26; N, 7.58.

Example 25

Preparation of $N^6$-tert-butyl phenoxyacetyl-5'-O-[2-(5-phenyl-2-nitrophenyl)-1-propyl oxycarbonyl]2'-deoxyadenosine (21) (Table 1)

Compound 21 was prepared according to the general method described in Example 23 using 2-(5-phenyl-2-nitrophenyl)-1-propyl oxycarbonylchloride (19a), to obtain a yellowish powder in 80% yield. $^1$H NMR (250 MHz, $CDCl_3$) δ 9.47 (br. d, 1H, NH), 8.74 and 8.19 (2d, 2H, H—C(2), H—C(8)), 7.85 (m, 1 arom. H), 7.61 (d, 1 arom. H), 7.52 (m, 2 arom. H), 7.43-7.30 (m, 4H, 2 arom. H protective gr.), 6.94 (d, 2 arom. H (tac)), 6.49 (t, 1H, H—C(1')), 4.80 (s, 2H, $CH_2$ (tac)), 4.67 (m, 1H, H—C(3')), 4.41-4.19 (m, 5H, 2×CH, H—C(5'), H—C(4')), 3.89 (m, 1H, CH (protective gr.)), 3.11 (br. s, 1H, HO-(3')), 2.80 (m, 1H, H—C(2')), 2.54 (m, 1H, H—C(2')), 1.41 (d, 3H, $CH_3$)), 1.27 (s, 9H, $CH_3$ (tert-butyl)). Elemental analysis for $C_{38}H_{40}N_6O_8 \times 1.5H_2O$ (734.78): calc.: C, 62.03; H, 5.89; N, 11.42. found: C, 62.27; H, 5.70; N, 11.39.

Example 26

Preparation of 5'-O-[2-(4-tert-butoxycarbonyl-2-nitrophenyl)-1-propyl oxycarbonyl]2'-deoxythymidine (25) (Table 1)

Compound 20 was prepared using the general method described in Example 17 starting with 2-(4-tert-butoxycarbonyl-2-nitrophenyl)-1-propyl oxycarbonylchloride (19e) to obtain a colorless powder in 72% yield. $^1$H NMR (250 MHz, $CDCl_3$) δ 8.89 (s, 1H, NH), 8.29 (s, 1H, arom. H(3) 4tBuOOCNPPOC), 8.14 (m, 1H, arom. H(5) 4tBuOOCNPPOC), 7.51 (m, 1H, arom. H(6) 4tBuOOCNPPOC), 7.27 (2×s, 1H, H—C(6)), 6.29 (m, 1H, H—C(1')), 4.45-4.08 (m, 6H, α-$CH_2$ 4tBuOOCNPPOC, 2×H—C(5'), H—C(3'), H—C(4')), 3.78 (sextet, 1H, 13-CH 4tBuOOCNPPOC), 2.87 (t, 1H, OH—C(3')), 2.34 (m, 1H, H—C(2')), 2.16 (m, 1H, H—C(2')), 1.85+1.79 (2×s, 3H, $CH_3$ thy), 1.58 (s, 9H, 3×$CH_3$ COOtBu), 1.36 (m, 3H, γ-$CH_3$ 4tBuOOCNPPOC).

Example 27

Preparation of $N^6$-benzoyl-5'-O-[2-(5-benzoyl-2-nitrophenyl)-1-propyl oxycarbonyl]2'-deoxyadenosine (29)

$N^6$-benzoyl-2'-deoxyadenosine (23.63 g, 67 mmol) was dried by coevaporation with abs. pyridine (3×100 mL), dissolved in pyridine (400 mL) and cooled to 0° C. A solution of 2-(5-benzoyl-2-nitrophenyl)-1-propyl oxycarbonylchloride (19f) (35 mmol, prepared from 10.00 g of alcohol 40 in abs. $CH_2Cl_2$ (100 mL) was added drop wise over a period of 2.5 hours. After stirring over night at ambient temperature the reaction mixture was concentrated in vacuo, dissolved in $CH_2Cl_2$ and washed with water (2×200 mL). Excess $N^6$-benzoyl-2'-deoxyadenosine precipitated as a crystalline solid from the aqueous phase and was recovered by filtration. The organic phase was diluted with toluene (100 mL), concentrated in vacuo and purified by silica column chromatography (315 g silica, column diameter 5.5 cm, gradient: $CH_2Cl_2$ to $CH_2Cl_2$/methanol 100:5) to provide 13.20 g (19.8 mmol, 57%) of the product 29 as a slightly yellow foam. $^1$H-NMR (250 MHz, DMSO-$d_6$): δ11.02 and 11.01 (2s, 2H, NH), 8.67 (s, 1H, H—C(2)), 8.51 and 8.50 (2s, 2H, H—C(8)), 8.00-7.48 (m, 13H, arom.), 6.46 (m, 1H, H—C(1')), 5.47 (d, 1H, HO—C(3')), 4.46 (m, 1H, H—C(3')), 4.28 (m, 4H, 2×$CH_2$), 4.03 (m, 1H, H—C(4')), 3.50 (m, β-CH), 2.86 (m, 1H, H—C(2'')), 2.40 (m, 1H, H—C(2')), 1.28 (d, 3H, γ-$CH_3$).

Example 28

Preparation of $N^4$-acetate-5'-O-[2-(5-benzoyl-2-nitrophenyl)-1-propyl oxycarbonyl]2'-deoxycytidine (30)

$N^4$-acetate-2'-deoxycytidine (17.87 g, 66 mmol) was dried by coevaporation with abs. pyridine (3×70 mL), dissolved in pyridine (200 mL) and cooled to 0° C. A solution of 2-(5-benzoyl-2-nitrophenyl)-1-propyl oxycarbonylchloride (19f) (35 mmol, prepared from 10.00 g of alcohol 4f) in abs. $CH_2Cl_2$ (100 mL) was added drop wise over a period of 2.5 hours. After stirring over night at ambient temperature the reaction mixture was concentrated in vacuo, dissolved in $CH_2Cl_2$ and washed with water (2×200 mL). The organic phase was diluted with toluene (100 mL), concentrated in vacuo and purified by silica column chromatography (320 g silica, column diameter 5.5 cm, gradient: $CH_2Cl_2$ to $CH_2Cl_2$/methanol 100:5) to provide 10.58 g (18.2 mmol, 52%) of the product 30 as a colourless foam. $^1$H-NMR (250 MHz, DMSO-$d_6$) δ 10.72 (s, 1H, NH), 7.96-7.50 (m, 9H, H—C(6) and arom.), 7.10 (d, 1H, H—C(5)), 7.09 (d, 1H, H—C(5)), 6.08 (m, 1H, H—C(1')), 5.37 (d, 1H, HO—C(3')), 4.32-4.22 (m, 4H, 2×$CH_2$), 4.15 (m, 1H, H—C(3')), 3.97 (m, 1H, H—C(4')), 3.54 (m, 1H, β-CH), 2.27 (m, 1H, H—C(2'')), 2.08 (s, 1H, NHAc), 2.05 (m, 1H, H—C(2')), 1.31 (d, 3H, γ-$CH_3$).

All of the other above described chlorocarbonates may be converted in an analogous way to the respective 5'- or 3'-protected nucleosides in excellent yields and sufficient purities.

Example 29

Preparation of 3'-O-[2-(5-phenyl-2-nitrophenyl)-1-propyl oxycarbonyl]2'-deoxythymidine (28)

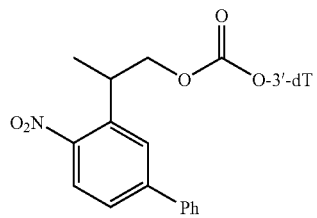

A solution of 2-(5-phenyl-2-nitrophenyl)-1-propanol (4a) (324.4 mg) and DMAP (36.1 mg) in acetonitrile (1 mL) was added to a solution of 3'-(4-nitrophenyl oxycarbonyl) 2'-deoxythymidine (102.7 mg, obtained by reacting 4-nitrophenyl oxycarbonyl chloride with 5'-dimethoxytrityl (DMT) protected 2'-deoxythymidine and subsequent removal of the DMT protective group under slightly acidic conditions (analogous to protocols well known in the art) in acetonitrile (1 mL). The mixture was stirred at ambient temperature for 20 minutes. The reaction was then quenched by adding $Na_2HPO_4/KH_2PO_4$ buffer (5 mL) and the mixture was extracted with dichloromethane (3×10 mL). The combined organic phases were dried over $Na_2SO_4$ and concentrated in vacuo. The crude product was purified by column chromatography on silica gel (8 g of silica, 16×1 cm, gradient: dichloromethane to dichloromethane:methanol 25:1). The product was obtained in 62.7% yield (82.9 mg) as slightly brown colored foam. $R_f$=0.20 ($CH_2Cl_2$/MeOH 20:1). $^1H$ NMR (250 MHz, $CDCl_3$) δ 8.61 (s, 1H, NH); 7.88 (d, 1H, arom. H protecting group); 7.62-7.37 (m, 8H, 7× arom. H protecting group, H—C (6)); 6.08 (m, 1H, H—C(1')); 5.25 (m, 1H, H—C(3')); 4.36 (m, 2H, α-$CH_2$); 4.08 (m, 1H, H—C(4')); 3.87 (m, 3H, 2×H—C(5'); β-CH protecting group); 2.54-2.15 (m, 3H, 2×H—C(2'); OH—C(5')); 1.89 (s, 3H, $CH_3$ Thy); 1.42 (d, 3H, $CH_3$ protecting group). UV ($λ_{max}$ [nm] (log ε); MeOH): 203 (4.64); 263 (4.22); [293 (3.92)]; 341, (3.78).

Example 30

General Protocol for the Preparation of 5'-O-photolabilely protected 3'-O-(β-cyanoethoxy,N,N-diisopropyl)phosphoramidityl 2'-deoxynucleosides The 5'-photolabilely protected 2'-deoxynucleoside (2 mmol) was suspended under argon in a mixture of abs. $CH_2Cl_2$ (8 mL) and abs. acetonitrile (2 mL). Tetrazole (140 mg, 2 mmol) and bis(diisopropylamino)-β-cyanoethoxy phosphane (1.2 g, 4 mmol) were then added. After stirring for 2.5 hours at room temperature $CH_2Cl_2$ (40 mL) was added and the resulting mixture was washed with a saturated aqueous solution of sodium bicarbonate (40 mL). The combined organic phase was dried and purified by silica column chromatography (EtOAc/$NEt_3$, 99:1 (v/v)). Products were obtained as amorphous solids in good yields.

Example 31

Preparation of 5'-O-[2-(5-phenyl-2-nitrophenyl)-1-propyl oxycarbonyl]2'-deoxythymidine-3'-O-(β-cyanoethoxy,N,N-diisopropyl) phosphoramidite The phosphoramidite was prepared according to the general procedure described in Example 30 to obtain a yellowish powder in 85% yield. $R_f$=0.83 and 0.79 (EtOAc, diastereomers). $^1H$ NMR (250 MHz, $CDCl_3$) δ 7.98 (br. s, NH), 7.87 (d, 1 arom. H), 7.61 (s, 1 arom. H), 7.57 (m, 3 arom. H), 7.45 (m, 3 arom. H), 7.26 (m, 1H, H—C(6)), 6.29 (t, 1H, HC(1')), 4.52-4.16 (m, 6H, 2×α-CH, H—C(5'), H—C(3'), H—C(4')), 3.89-3.50 (m, 5H, O—$CH_2CH_2CN$, β-CH, 2×CH(isopropyl)), 2.61 (m, 2H, $CH_2CN$), 2.40 (m, 1H, H—C(2')), 2.13 (m, 1H, H—C(2')), 1.80-1.72 (m, 3H, $CH_3$-thy)), 1.41 (d, 3H, $CH_3$), 1.15 (m, 12H, 4×$CH_3$ (isopropyl)).

Example 32

Preparation of $N^6$-tert-butylphenyloxyacetyl-5'-O-[2-(5-phenyl-2-nitrophenyl)-1-propyl oxycarbonyl]2'-deoxyadenosine-3'-O-(β-cyanoethoxy,N,N-diisopropyl)phosphoramidite The phosphoramidite was prepared according to general method described in Example 30 to obtain 80% yield of a yellowish powder. $R_f$=0.77 and 0.67 (EtOAc, diastereomers). $^1H$ NMR (250 MHz, $CDCl_3$) δ 9.38 (s (br.), 1H, NH), 8.76 and 8.18 (2d, 2H, H—C(2), H—C(8)), 7.87 (dd, 1H, arom. H), 7.53 (m, 3H, 1 arom. H, 2 arom. H (tac)), 7.40 (m, 3×arom. H), 7.32 (m, 2×arom. H), 6.95 (m, 2×arom. H (tac)), 6.47 (m, 1H, H—C(1')), 4.79 (s, 2H, $CH_2$ (tac)), 4.68 (m, 1H, H—C (3')), 4.33 (m, 5H, 2×α-CH, 2×H—C(5'), H—C(4')), 3.89-3.52 (m, 5H, O—$CH_2CH_2$, β-CH, 2×CH (isopropyl)), 2.84 (m, 1H, H—C(2')), 2.63 (m, 3H, $CH_2CN$, H—C(2')), 1.42 (d, 3H, $CH_3$), 1.27 (s, 9H, 3×$CH_3$ (tert-butyl)), 1.15 (m, 12H, 4×$CH_3$ (isopropyl)). $^{31}$P-NMR (400 MHz, $CDCl_3$) δ 146.70, 146.65 and 146.56 (3×s, diastereomers).

Example 33

Preparation of 5'-O-[2-(4-tert-butoxycarbonyl-2-nitrophenyl)-1-propyl oxycarbonyl]2'-deoxy thymidine-3'-O-(β-cyanoethyl, N,N-diisopropyl) phosphoramidite Prepared according to the general method described in Example 30 to obtain a colorless powder in 86% yield. $R_f$=0.83 and 0.77 (EtOAc/hexane 9:1, diastereomers). $^1H$ NMR (250 MHz, $CDCl_3$) δ 8.29 (s, 1H, arom. H 4tBuOOC-NPPOC), 8.14 (m, 2H, arom. H 4tBuOOCNPPOC, NH), 7.51 (d, 1H, arom. H 4tBuOOCNPPOC), 7.27 (dd, 1H, H—C(6)), 6.30 (m, 1H, H—C(1')), 4.50-4.17 (m, 6H, H—C(3'), 2×H—C(5'), 2×α-CH 4tBuOOCNPPOC, H—C(4')), 3.84-3.52 (m, 5H, α-$CH_2$ CE, β-CH 4tBuOOCNPPOC, 2×CH iPr), 2.61 (m, 2H, β-$CH_2$ CE), 2.43 (m, 1H, H—C(2')), 2.15 (m, 1H, H—C(2')), 1.85, 1.80, 1.79+1.78 (4×s, 3H, $CH_3$ thy), 1.58 (s, 9H, 3×$CH_3$ COOtBu), 1.36 (dd, 3H, β-$CH_3$ 4tBuOOCNP-POC), 1.18, 1.17, 1.15 u. 1.14 (4×s, 12H, 4×$CH_3$ iPr). $^{31}$P-NMR (400 MHz, DMSO-$d_6$) δ 148.66, 148.53+148.44

Example 34

Preparation of 3'-O-[2-(5-phenyl-2-nitrophenyl)-1-propyl oxycarbonyl]2'-deoxythymidine-5'-O-(β-cyanoethoxy,N,N-diisopropyl) phosphoramidite Bis(diisopropylamino)-β-cyanoethoxy phosphane (121 mg) was added to a solution of 3'-O-[2-(5-phenyl-2-nitrophenyl)-1-propyl oxycarbonyl]2'-deoxythymidine (140 mg) and DCI (16 mg) in dichloromethane (3 mL). The reaction mixture was stirred at ambient temperature for 30 minutes. The mixture was diluted with dichloromethane (30 mL) and washed with a saturated aq. solution of NaHCO$_3$ (15 mL). The organic phase was separated, dried over Na$_2$SO$_4$ and concentrated in vacuo. The residue was dissolved in dichloromethane (2 mL) and poured into n-hexane (50 mL) to precipitate the product. The precipitate was separated, dissolved in a small volume of dichloromethane and purified by chromatography (5.5 g of silica, 12×0.8 cm, gradient: n-hexane/acetone 4:1 to 1:1). The product was obtained in 51.6% yield (100 mg) as a colorless foam. R$_f$=0.32 (hexane/acetone 7:5). $^1$H NMR (400 MHz, DMSO) δ 11.37 (s, 1H, NH); 7.95-7.43 (m, 9H, arom. H+H—C(6)); 6.13-6.05 (m, 1H, H—C(1')); 5.10-5.04 (m, 1H, H—C(3')); 4.43-4.41 (m, 2H, H—C(5')); 4.12-4.05 (m, 1H, H—C(4')); 3.78-3.29 (m, 9H, 3×O—CH$_2$, H—C—CH$_3$, β-CH isopropyl); 2.77-2.72 (m, 2H, CNC̄H$_2$); 2.27 (m, 2H, H—C(2')); 1.77 (s, 1H, C H$_3$-Thy); 1.35 (d, 3H, CH$_3$); 1.14-1.04 (m, 12H, CH$_3$ isopropyl). $^{31}$P-NMR (400 MHz, DMSO): δ 151.66.

Example 35

Preparation of N$^6$-benzoyl-5'-O-[2-(5-benzoyl-2-nitrophenyl)-1-propyl oxycarbonyl]2'-deoxyadenosine-3'-O-(β-cyanoethoxy,N,N-diisopropyl)phosphoramidite Bis(diisopropylamino)-β-cyanoethoxy phosphane (8.50 g, 28 mmol) was added to a solution of N$^6$-benzoyl-5'-O-[2-(5-benzoyl-2-nitrophenyl)-1-propyl oxycarbonyl]2'-deoxyadenosine (12.50 g, 19 mmol) and DCI (1.11 g, 9 mmol) in dichloromethane (130 mL). The reaction mixture was stirred at ambient temperature for 3 hours. The mixture was then diluted with hexane (120 mL) and filtered through a silica bed in a column (42 g silica, diameter 3 cm). The column was eluted with a gradient of hexane/ethyl acetate (1:1, v/v) to ethyl acetate. The product fractions were concentrated in vacuo to a volume of approx. 200 mL and then poured slowly into hexane (1.5 L) under vigorous stirring to precipitate the product. The precipitate was separated, dissolved in a small volume of ethyl acetate and precipitated a second time in the same manner. The precipitate was again separated, dissolved in dichloromethane and concentrated in vacuo to provide the product in 88% (14.45 g) as a colorless foam. $^{31}$P-NMR (400 MHz, DMSO-d$_6$) δ 148.88, 148.78.

Example 36

Preparation of N$^4$-acetyl-5'-O-[2-(5-benzoyl-2-nitrophenyl)-1-propyl oxycarbonyl]2'-deoxycytidine-3'-O-(β-cyanoethoxy,N,N-diisopropyl)phosphoramidite Bis(diisopropylamino)-β-cyanoethoxy phosphane (7.69 g, 26 mmol) was added to a solution of N$^4$-acetyl-5'-O-[2-(5-benzoyl-2-nitrophenyl)-1-propyl oxycarbonyl]2'-deoxycytidine (9.89 g, 17 mmol) and DCI (1.00 g, 9 mmol) in dichloromethane (100 mL). The reaction mixture was stirred at ambient temperature for 3 hours. The mixture was then diluted with hexane (120 mL) and filtered through a silica bed in a column (43 g silica, diameter 3 cm). The column was eluted with a gradient of hexane/ethyl acetate (1:1, v/v) to ethyl acetate. The product fractions were concentrated in vacuo to a volume of approx. 100 mL and then poured slowly into hexane (1.5 L) under vigorous stirring to precipitate the product. The precipitate was separated, dissolved in a small volume of ethyl acetate and precipitated a second time in the same manner. The precipitate was again separated, dissolved in dichloromethane and concentrated in vacuo to give the product in 88% (11.69 g) as a colorless foam. $^{31}$P-NMR (400 MHz, DMSO-d$_6$) δ 149.00.

Example 37

Deprotection Studies in Solution

Compounds to be photolyzed in solution were dissolved either in 1:1 (v/v) or 95:5 (v/v) mixtures of methanol/water and acetonitrile/water, respectively, at 0.1 to 0.3 mM concentrations. Due to their lower solubility all guanosine derivatives were dissolved in 3:2 (v/v) instead of 1:1 (v/v) mixtures of methanol or acetonitrile in water. In a 10 mm path length quartz cuvette the solutions were exposed to a collimated super high pressure mercury lamp (Osram Sylvania Inc., Danvers, Mass.) as a light source (200 W) equipped with a polarization filter, an UV-filter to provide for a narrow spectral band at the desired wavelength of 365 nm, and an electronic shutter to ensure exact exposure times. During the measurements the solutions were adjusted to 17° C. and mixed with a magnetic stirrer. For each time period of exposure a 3 mL aliquot was employed and afterwards analyzed by reversed phase HPLC (20 to 100% CH$_3$CN over 30 minutes, photometric detection at 260 nm). The primary photolysis products were identified by co-injecting authentic standards, photolysis was followed by monitoring the disappearance of starting material, and half-times were calculated by plotting the peak area values versus the time, using linear regression analysis. The results for several nucleosides bearing different photolabile protective groups are depicted in the Tables 1, 2 and 3.

Example 38

Deprotection Studies in the Dry State

Compounds to be photolyzed in the dry state were first dissolved in an appropriate solvent to give 1 mM solutions. 5 µL of each solution were pipetted onto a polystyrene surface and the solvent was removed. The dried compounds were then irradiated directly employing a set-up analogous to that described in Example 37, but without a polarization filter and a 100 W high pressure mercury lamp (Osram Sylvania Inc., Danvers, Mass.). Samples of every compound were exposed for different time periods and the resulting amounts of the educt and deblocked nucleoside were determined by HPLC as described in Example 37. The results obtained for a series of differently protected deoxythymidines are set forth in FIG. 2, which displays the rate of photolyltic decay of the protected deoxythymidines and FIG. 3, which displays the rate of formation of the deoxythymidines.

Example 39

Silanization of Glass Slides

Erie Gold seal microscope slides (Fisher, Hanover Park, Ill.), arranged in odd-numbered slots of a stainless-steel slide rack, were incubated in an aqueous sodium hydroxide solution (10%, w/v) for 10 minutes at room temperature. The slides were then rinsed in two dishes of deionized water (for 2.5 minutes in each bath). After rinsing, the slides were transferred to an aqueous bis(2 hydroxyethyl)-aminopropyltriethoxysilane solution (2%, v/v) (United Chemical Technologies, Bristol, Pa.) with shaking for 1 hour. After the silane coating, the slides were rinsed in 95% ethanol for 5 minutes. The slides were then dipped immediately into ether and air dried. Once the slides were completely dry, they were baked for 15 minutes at 100° C. Immediately after baking the slides were stored in a desiccated at −20° C.

Example 40

On-Chip Deprotection Studies in Solution

Customized arrays were designed to study the deprotection rates for the inventive protective groups as compared to the prior art photolabile protective groups MeNPOC and NPPOC, with and without the addition of sensitizers to the exposure solvent. The arrays were prepared as described in Example 40 with a single cycle of DNA synthesis to the silanized slide after which defined areas received varying doses of illumination. Cy3 amidite (Amersham Pharmacia, Piscataway, N.J.) was coupled to the array to provide a relative measure of free hydroxyl groups. The array was then removed and placed in deprotection solution, ethylenediamine/ethanol (1:1, v/v) for 2 hours. The arrays were then scanned on an Axon 4000B (Axon Instruments, Union City, Calif.).

Example 41

On-Chip Deprotection Studies in the Dry State

These experiments were carried out as described in Example 41, with the exception that prior to the illumination in the course of the deprotection step all solvent was removed from the flow cell and the support was dried with an argon stream.

Example 42

Array Synthesis

Standard DNA synthesis reagents (Glen Research (Sterling, Va.) and Proligo (Boulder, Colo.) were used on Expedite DNA synthesizers (Applied Biosystems, Foster City, Calif.). The NPPOC protected phosphoramidites (5'-NPPOC-deoxyadenosine [N6-tac] β-cyanoethoxy phosphoramidite, 5'-NPPOC-deoxycytidine [N4-isobutyryl] β-cyanoethoxy phosphoramidite, 5'-NPPOC-deoxyguanosine [N2-ipac] β-cyanoethoxy phosphoramidite, 5'-NPPOC-deoxythymidine β-cyanoethoxyphosphoramidite) were obtained from Proligo, whereas the phosphoramidites comprising the inventive protective groups were synthesized as described above. The MAS unit (NimbleGen Systems, Madison, Wis.) was connected via a flow cell containing the support to the Expedite to manufacture the customized arrays. Arrays were designed with JazzSuite software (NimbleGen Systems). After synthesis on the MAS was completed, the base-protecting groups were removed in a solution of ethylenediamine/ethanol (1:1 v/v; Aldrich) for 2 hours. The arrays were rinsed with water, dried, and stored desiccated until use.

TABLE 1

Photolysis half-lives of 5'-NPPOC protected deoxynucleosides compared to the known NPPOC-group, measured in aqueous methanolic solutions as described in Example 37.

| Entry | Compound | $t_{1/2}$ (seconds) |
|---|---|---|
| 1. | 20 | 17 |
| 2. | 21 | 19 |
| 3. | 22 | 18 |
| 4. | 23 | 19 |
| 5. | 24 | 77 |
| 6. | 25 | 75 |

TABLE 1-continued

Photolysis half-lives of 5'-NPPOC protected deoxynucleosides compared to the known NPPOC-group, measured in aqueous methanolic solutions as described in Example 37.

| Entry | Compound | $t_{1/2}$ (seconds) |
|---|---|---|
| 7. | (structure 26) | 54 |

TABLE 2

Photolysis half-lives of 5'-NPPOC protected deoxynucleosides, compared to the known NPPOC-group, measured in aqueous acetonitrile solutions as described in Example 37.

| Entry | Compound | $t_{1/2}$ (seconds) |
|---|---|---|
| 1. | (structure 20) | 15 |
| 2. | (structure 21) | 15 |
| 3. | (structure 22) | 15 |
| 4. | (structure 23) | 17 |

TABLE 2-continued

Photolysis half-lives of 5'-NPPOC protected deoxynucleosides, compared to the known NPPOC-group, measured in aqueous acetonitrile solutions as described in Example 37.

| Entry | Compound | $t_{1/2}$ (seconds) |
|---|---|---|
| 5. | (structure 26) | 58 |

TABLE 3

Photolysis half-lives 5'-Bz NPPOC protected deoxynucleosides compared to the respective half live of NPPOC-dT (26), measured in aqueous methanol and acetonitrile solutions, respectively, as described in Example 37

| Entry | Compound | Solvent | $t_{1/2}$ (seconds) |
|---|---|---|---|
| 1 | 5'-Bz-NPPOC-dT (28) | methanol with 5% $H_2O$ | 1.9 |
|   |   | acetonitrile with 5% $H_2O$ | 1.8 |
| 2 | 5'-Bz-NPPOC-dA(bz) (29) | methanol with 5% $H_2O$ | 2.4 |
|   |   | acetonitrile with 5% $H_2O$ | 1.9 |
| 3 | 5'-Bz-NPPOC-dC(ac) (30) | methanol with 5% $H_2O$ | 1.8 |
|   |   | acetonitrile with 5% $H_2O$ | 1.5 |
| 4 | 5'-(2-Fluor-Bz)-NPPOC-dT (31) | methanol with 5% $H_2O$ | 1.9 |
|   |   | acetonitrile with 5% $H_2O$ | 1.7 |
| 5 | 5'-(3-Fluor-Bz)-NPPOC-dT (32) | methanol with 5% $H_2O$ | 1.6 |
|   |   | acetonitrile with 5% $H_2O$ | 1.9 |
| 6 | 5'-(4-Fluor-Bz)-NPPOC-dT (33) | methanol with 5% $H_2O$ | 1.6 |
|   |   | acetonitrile with 5% $H_2O$ | 2.0 |
| 7 | 5'-NPPOC-dT (26) | methanol with 5% $H_2O$ | 5.0 |

TABLE 4

Photolysis half-lives of 5'-Bz NPPOC protected deoxynucleosides compared to the respective half live of NPPOC-dT (26), measured under dry conditions as described in Example 38.

| Entry | Compound | $t_{1/2}$ (seconds) |
|---|---|---|
| 1 | 5'-Bz-NPPOC-dT (28) | 6.0 |
| 2 | 5'-Bz-NPPOC-dA(bz) (29) | 6.0 |
| 3 | 5'-Bz-NPPOC-dC(ac) (30) | 6.0 |
| 4 | 5'-(2-Fluor-Bz)-NPPOC-dT (31) | 6.0 |
| 5 | 5'-(3-Fluor-Bz)-NPPOC-dT (32) | 6.0 |
| 6 | 5'-(4-Fluor-Bz)-NPPOC-dT (33) | 7.8 |
| 7 | 5'-NPPOC-dT (26) | 14.0 |

TABLE 5

Average cycle yields for support bound $dT_{12}$ arrays prepared as described in Example 40 and using the dry deprotection protocol of Example 42

| 5'-protective group | exposure time (seconds) | average cycle yield (%) |
|---|---|---|
| Bz-NPPOC | 18 | 86 |
|   | 35 | 90 |
| NPPOC | 65 | 81 |
| MeNPOC | 58 | 86 |

The invention claimed is:

1. A compound having the following general formula:

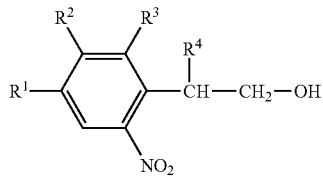

wherein
$R^1$ is selected from the group consisting of H, $NO_2$, CN, $OCH_3$, a halogen, an alkyl group having up to 4 carbon atoms and an alkoxyl group having up to 4 carbon atoms, and $R^2$ is selected from the group consisting of an optionally substituted aryl group, an optionally substituted heteroaryl group and an optionally substituted aroyl group;
and wherein
$R^3$ is selected from the group consisting of H, $NO_2$ and halogen; and
$R^4$ is selected from the group consisting of H, $OCH_3$ and an alkyl group having up to 4 carbon atoms,
wherein the optionally substituted aryl group, optionally substituted heteroaryl group and optionally substituted aroyl group may be substituted with 1 to 3 substituents selected from the group consisting of an alkyl group, an alkoxyl group, a halogen atom, a hydroxyl group, an amino group, an acyl group, a nitro group, a cyano group, and a thioalkyl group.

2. The compound of claim 1, wherein the compound is 2-(5-phenyl-2-nitrophenyl)propanol.

3. The compound of claim 1, wherein $R^1$ is hydrogen, $R^2$ is an optionally substituted phenyl or benzoyl moiety, $R^3$ is hydrogen, and $R^4$ is a methyl group.

4. The compound of claim 1, wherein $R^1$ is $NO_2$, $R^2$ is an optionally substituted phenyl or benzoyl moiety, $R^3$ is H or a halogen, and $R^4$ is a methyl group.

5. The compound of claim 1, wherein $R^1$ is selected from the group consisting of H, CN, $OCH_3$, a halogen, an alkyl group having up to 4 carbon atoms and an alkoxyl group having up to 4 carbon atoms, $R^2$ is an optionally substituted phenyl or benzoyl moiety, $R^3$ is $NO_2$, and $R^4$ is a methyl group.

6. The compound of claim 1, wherein $R^1$ and $R^2$ are at least one alkyl group having up to 4 carbon atoms.

7. The compound of claim 6, wherein the $R^1$ group is an alkoxyl group having up to 4 carbon atoms.

8. The compound of claim 1, $R^2$ is at least one of a phenyl group, a methoxy phenyl group and a naphthalene group.

9. The compound of claim 1, wherein $R^2$ is at least one of an aryl group, a substituted aryl group, a heteroaryl group, a substituted heteroaryl group, an aroyl group and a substituted aroyl group.

10. The compound of claim 1, wherein
$R^1$ is selected from the group consisting of H, $NO_2$, CN, $OCH_3$, a halogen, an alkyl group having up to 4 carbon atoms and an alkoxyl having up to 4 carbon atoms, and $R^2$ is selected from the group consisting of an aryl group, a substituted aryl group, a heteroaryl group, a substituted heteroaryl group, an aroyl group and a substituted aroyl group; and
$R^3$ is selected from the group consisting of H, $NO_2$ and halogen; and
$R^4$ is selected from the group consisting of H, $OCH_3$ and an alkyl group having up to 4 carbon atoms.

11. A method for the preparation of a derivatized nucleoside or nucleoside analog thereof comprising:
a) reacting an alcohol having the formula 4:

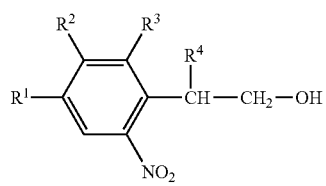

wherein
$R^1$ is selected from the group consisting of H, $NO_2$, CN, $OCH_3$, a halogen, an alkyl group having up to 4 carbon atoms and an alkoxyl group having up to 4 carbon atoms, under the proviso that $R^2$ is selected from the group consisting of an optionally substituted aryl group, an optionally substituted heteroaryl group and an optionally substituted aroyl group;
$R^3$ is selected from the group consisting of H, $NO_2$ and halogen; and
$R^4$ is selected from the group consisting of H, $OCH_3$ and an alkyl group having up to 4 carbon atoms,
wherein the optionally substituted aryl group, optionally substituted heteroaryl group and optionally substituted aroyl group may be substituted with 1 to 3 substituents selected from the group consisting of an alkyl group, an alkoxyl group, a halogen atom, a hydroxyl group, an amino group, an acyl group, a nitro group, a cyano group, and a thioalkyl group; and
with phosgene diphosgene, triphosgene, carbonyldiimidazole, bis-nitrophenyl carbonate, nitrophenoxy carbonyl chloride and pentafluorophenoxy chloroformate, or with the respective thiocarbonyl compound, to produce an activated carbonate ester or thiocarbonate ester and
b) reacting the activated carbonate or thiocarbonate ester as formed in a) with a nucleoside of the general formula (5):

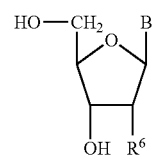

wherein
$R^6$ is selected from the group consisting of H, OH, an alkoxy group having up to 4 carbon atoms and an alkenoxyl group having up to 4 carbon atoms, or $WR^8$ wherein W is oxygen or sulfur and $R^8$ is a dimethoxytrityl protective group or a silyl ether protective group and
B is selected from the group consisting of adenine, cytosine, guanine, thymine, and uracil and in the case of adenosine, cytosine and guanine the amino functions on the heterocycle may optionally bear a dimethoxytrityl protective group or a silyl ether protective group;

or with a nucleoside selected from the group of compounds of general formula (6):

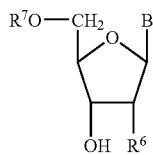

(6)

wherein $R^6$ is selected from the group consisting of H, OH, an alkoxyl group having up to 4 carbon atoms and an alkenoxyl group having up to 4 carbon atoms, and $WR^8$ wherein W is oxygen or sulfur and $R^8$ is a dimethoxytrityl protective group or a silyl ether protective group; and $R^7$ is a dimethoxytrityl protective group or a silyl ether protective group;

B is selected from the group consisting of adenosine, adenine, cytosine, guanine, thymine, and uracil, which may optionally bear a dimethoxytrityl protective group or a silyl ether protective group;

c) optionally removing the dimethoxytrityl protective group or the silyl ether protective group and purifying the product; and d) reacting the product from b) or c) with a phosphitylation reagent to provide a phosphoramidite.

12. The method of claim 11 wherein said phosphitylation reagent is bis(diisopropylamino)-β-cyanoethoxy phosphane.

13. A method for the preparation of a derivatized nucleoside or nucleoside analog thereof comprising:

a) reacting a nucleoside of general formula (5):

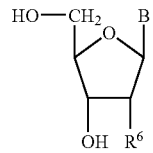

(5)

wherein $R^6$ is selected from the group consisting of H, OH, an alkoxyl group having up to 4 carbon atoms and an alkenoxyl group having up to 4 carbon atoms, or $WR^8$ wherein W is oxygen or sulfur and $R^8$ is a dimethoxytrityl or silyl ether protective group and B is selected from the group consisting of adenine, cytosine, guanine, thymine, and uracil and in the case of adenosine, cytosine and guanine the amino functions on the heterocycle may optionally bear a dimethoxytrityl or silyl ether protective group;

or a nucleoside of general formula (6):

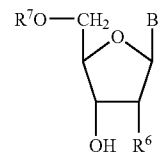

(6)

wherein $R^6$ is selected from the group consisting of H, OH, an alkoxyl group having up to 4 carbon atoms and an alkenoxyl group having up to 4 carbon atoms, or $WR^8$ wherein W is oxygen or sulfur and $R^8$ is a dimethoxytrityl or silyl ether protective group and $R^7$ is a dimethoxytrityl or silyl ether protective group; and B is selected from the group consisting of adenosine, adenine, cytosine, guanine, thymine, and uracil, that may optionally bear a dimethoxytrityl protective group or a silyl ether protective group;

with phosgene diphosgene, triphosgene, carbonyldiimidazole, bis-nitrophenyl carbonate, nitrophenoxy carbonyl chloride and pentafluorophenoxy chloroformate, or with the respective thiocarbonyl compound, to produce an activated carbonate ester or thiocarbonate ester;

b) reacting the activated carbonate or thiocarbonate ester as formed in a) with an alcohol having the general formula 4:

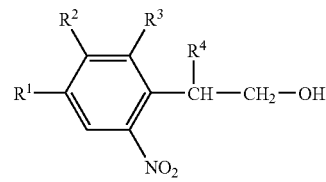

(4)

wherein $R^1$ is selected from the group consisting of H, $NO_2$, CN, $OCH_3$, a halogen an alkyl group having up to 4 carbon atoms and an alkoxyl group respectively, having up to 4 carbon atoms, under the proviso that $R^2$ is selected from the group consisting of an optionally substituted aryl group, an optionally substituted heteroaryl group and an optionally substituted aroyl group;

$R^3$ is selected from the group consisting of H, $NO_2$ and halogen; and $R^4$ is selected from the group consisting of H, $OCH_3$ and an alkyl group having up to 4 carbon atoms, wherein the optionally substituted aryl group, optionally substituted heteroaryl group and optionally substituted aroyl group may be substituted with 1 to 3 substituents selected from the group consisting of an alkyl group, an alkoxyl group, a halogen atom, a hydroxyl group, an amino group, an acyl group, a nitro group, a cyano group, and a thioalkyl group; and c) optionally removing the dimethoxytrityl protective group or the silyl ether protective group and purifying the product; and d) reacting the product from b) or c) with a phosphitylation reagent to provide a phosphoramidite.

14. The method of claim 13 wherein said phosphitylation reagent is bis(diisopropylamino)-β-cyanoethoxy phosphane.

15. A method for a light-controlled oligonucleotide synthesis comprising:
subjecting a composition comprising the phosphoramidites of claim 11 to a light-controlled oligonucleotide synthesis.

16. The method of claim 15, wherein the light controlled oligonucleotide synthesis is effected on a solid support.

17. A method for a light-controlled oligonucleotide synthesis comprising:
subjecting a composition comprising the phosphoramidites of claim 13 to a light controlled oligonucleotide synthesis.

18. A method for derivatizing an oligonucleotide, said method comprising reacting said oligonucleotide with a compound of general formula (1):

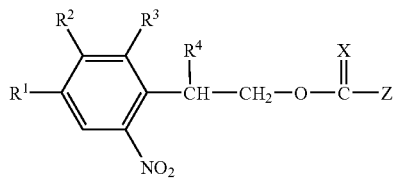

wherein the oligonucleotide comprises a primary amine, a secondary amine, or a hydroxyl group, $R^1$ is selected from the group consisting of H, $NO_2$, CN, $OCH_3$, a halogen, an optionally substituted alkyl group having up to 4 carbon atoms and an alkoxyl group respectively, having up to 4 carbon atoms, under the proviso that $R^2$ is selected from the group consisting of an optionally substituted aryl group, an optionally substituted heteroaryl group and an optionally substituted aroyl group;

$R^3$ is selected from the group consisting of H, $NO_2$ and halogen;

$R^4$ is selected from the group consisting of H, $OCH_3$ and an alkyl group having up to 4 carbon atoms, wherein the optionally substituted aryl group, optionally substituted heteroaryl group and optionally substituted aroyl group may be substituted with 1 to 3 substituents selected from the group consisting of an alkyl group, an alkoxyl group, a halogen atom, a hydroxyl group, an amino group, an acyl group, a nitro group, a cyano group, and a thioalkyl group; and X is oxygen or sulfur; and Z is a leaving group selected from the group consisting of a (thio)carbamate, a (thio)carbonate, a halide, an imidazolyl group, and a nitrophenoxyl group.

19. A method for removing a photolabile protective group having the following formula:

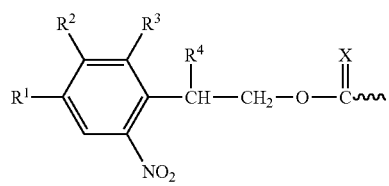

$R^1$ is selected from the group consisting of H, $NO_2$, CN, $OCH_3$, a halogen, an alkyl group having up to 4 carbon atoms and an alkoxyl group having up to 4 carbon atoms, under the proviso that $R^2$ is selected from the group consisting of an optionally substituted aryl group, an optionally substituted heteroaryl group and an optionally substituted aroyl group;

$R^3$ is selected from the group consisting of H, $NO_2$ and halogen;

$R^4$ is selected from the group consisting of H, $OCH_3$ and an alkyl group having up to 4 carbon atoms;

wherein the optionally substituted aryl group, optionally substituted heteroaryl group and optionally substituted aroyl group may be substituted with 1 to 3 substituents selected from the group consisting of an alkyl group, an alkoxyl group, a halogen atom, a hydroxyl group, an amino group, an acyl group, a nitro group, a cyano group, and a thioalkyl group; and X is oxygen or sulfur;

said method comprising irradiating an oligonucleotide having said photolabile protective group with light.

* * * * *